(12) United States Patent
Ghosh

(10) Patent No.: US 10,596,383 B2
(45) Date of Patent: Mar. 24, 2020

(54) FEATURE BASED SENSING FOR LEADLESS PACING THERAPY

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 192 days.

(21) Appl. No.: 15/944,050

(22) Filed: Apr. 3, 2018

(65) Prior Publication Data

US 2019/0299012 A1 Oct. 3, 2019

(51) Int. Cl.
A61N 1/368 (2006.01)
A61N 1/375 (2006.01)
A61N 1/37 (2006.01)
A61N 1/365 (2006.01)
A61N 1/362 (2006.01)
A61N 1/39 (2006.01)
(Continued)

(52) U.S. Cl.
CPC ......... A61N 1/3756 (2013.01); A61N 1/3621 (2013.01); A61N 1/36507 (2013.01); A61N 1/3712 (2013.01); A61N 1/056 (2013.01); A61N 1/3627 (2013.01); A61N 1/3688 (2013.01); A61N 1/37288 (2013.01); A61N 1/3956 (2013.01)

(58) Field of Classification Search
None
See application file for complete search history.

(56) References Cited

U.S. PATENT DOCUMENTS 4,280,502 A 7/1981 Baker, Jr. et al.
4,374,382 A 2/1983 Markowitz
4,787,389 A 11/1988 Tarjan
(Continued)

FOREIGN PATENT DOCUMENTS

EP 0728497 B1 12/2002
EP 1541191 A1 6/2005
(Continued)

OTHER PUBLICATIONS (PCT/US2014/066792) PCT Notification of Transmittal of the International Search Report and the Written Opinion of the International Searching Authority.
(Continued)

Primary Examiner — Brian T Gedeon

(57) ABSTRACT

A method and system that includes an implantable cardioverter defibrillator (ICD) determining signal characteristics of a cardiac signal within a signal evaluation window positioned along a first portion of a cardiac cycle and determining whether a P-wave occurs within the signal evaluation window associated with the first portion of the cardiac cycle. The signal evaluation window is adjusted to be positioned along a second portion of the cardiac cycle in response to the P-wave not occurring within the signal evaluation window and signal characteristics of the cardiac signal are determined within the adjusted signal evaluation window. A determination is made as to whether a P-wave occurs in response to the signal characteristics determined within the adjusted signal evaluation window, and the ICD delivers a trigger signal to a leadless pacing device instructing delivery of ventricular pacing therapy by the leadless pacing device whenever a P-wave is determined to occur.

23 Claims, 7 Drawing Sheets

(51) Int. Cl.
  *A61N 1/05* (2006.01)
  *A61N 1/372* (2006.01)

(56) References Cited

U.S. PATENT DOCUMENTS

| | | |
|---|---|---|
| 4,830,006 A | 5/1989 | Haluska et al. |
| 4,865,037 A | 9/1989 | Chin et al. |
| 5,117,824 A | 6/1992 | Keimel et al. |
| 5,144,950 A | 9/1992 | Stoop et al. |
| 5,174,289 A | 12/1992 | Cohen |
| 5,193,539 A | 3/1993 | Schulman et al. |
| 5,255,692 A | 10/1993 | Neubauer et al. |
| 5,318,594 A | 6/1994 | Limousin et al. |
| 5,507,782 A | 4/1996 | Kieval et al. |
| 5,683,426 A | 11/1997 | Greenhut et al. |
| 5,749,909 A | 5/1998 | Schroeppel et al. |
| 5,814,089 A | 9/1998 | Stokes et al. |
| 5,817,130 A | 10/1998 | Cox et al. |
| 5,928,271 A | 7/1999 | Hess et al. |
| 6,256,534 B1 | 7/2001 | Dahl |
| 6,393,316 B1 | 5/2002 | Gillberg et al. |
| 6,442,426 B1 | 8/2002 | Kroll |
| 6,508,771 B1 | 1/2003 | Padmanabhan et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,597,951 B2 | 7/2003 | Kramer et al. |
| 6,622,046 B2 | 9/2003 | Fraley et al. |
| 6,721,597 B1 | 4/2004 | Bardy et al. |
| 6,754,528 B2 | 6/2004 | Bardy et al. |
| 6,788,971 B1 | 9/2004 | Sloman et al. |
| 6,871,096 B2 | 3/2005 | Hill |
| 6,904,315 B2 | 6/2005 | Panken et al. |
| 6,934,585 B1 | 8/2005 | Schloss et al. |
| 6,993,389 B2 | 1/2006 | Ding et al. |
| 7,013,176 B2 | 3/2006 | Ding et al. |
| 7,181,284 B2 | 2/2007 | Burnes et al. |
| 7,231,248 B2 | 6/2007 | Kramer et al. |
| 7,231,253 B2 | 6/2007 | Tidemand et al. |
| 7,272,448 B1 | 9/2007 | Morgan et al. |
| 7,558,626 B2 | 7/2009 | Corbucci |
| 7,610,092 B2 | 10/2009 | Cowan et al. |
| 7,630,764 B2 | 12/2009 | Ding et al. |
| 7,634,313 B1 | 12/2009 | Kroll et al. |
| 7,657,313 B2 | 2/2010 | Rom |
| 7,706,879 B2 | 4/2010 | Burnes et al. |
| 7,761,150 B2 | 7/2010 | Ghanem et al. |
| 7,848,815 B2 | 12/2010 | Brisken et al. |
| 7,877,144 B2 | 1/2011 | Coles, Jr. et al. |
| 7,881,791 B2 | 2/2011 | Sambelashvili et al. |
| 7,890,173 B2 | 2/2011 | Brisken et al. |
| 7,894,902 B2 | 2/2011 | Rom |
| 7,912,544 B1 | 3/2011 | Min et al. |
| 7,930,027 B2 | 4/2011 | Prakash et al. |
| 7,937,148 B2 | 5/2011 | Jacobson |
| 7,941,218 B2 | 5/2011 | Sambelashvili et al. |
| 7,953,493 B2 | 5/2011 | Fowler et al. |
| 7,991,467 B2 | 8/2011 | Markowitz et al. |
| 7,996,087 B2 | 8/2011 | Cowan et al. |
| 8,002,718 B2 | 8/2011 | Buchholtz et al. |
| 8,032,219 B2 | 10/2011 | Neumann et al. |
| 8,046,065 B2 | 10/2011 | Burnes et al. |
| 8,145,308 B2 | 3/2012 | Sambelashvili et al. |
| 8,204,590 B2 | 6/2012 | Sambelashvili et al. |
| 8,214,041 B2 | 7/2012 | Van Gelder et al. |
| 8,315,701 B2 | 11/2012 | Cowan et al. |
| 8,321,014 B2 | 11/2012 | Maskara et al. |
| 8,352,027 B2 | 1/2013 | Spinelli et al. |
| 8,391,964 B2 | 3/2013 | Musley et al. |
| 8,428,716 B2 | 4/2013 | Mullen et al. |
| 8,433,409 B2 | 4/2013 | Johnson et al. |
| 8,457,742 B2 | 6/2013 | Jacobson |
| 8,467,871 B2 | 6/2013 | Maskara |
| 8,521,268 B2 | 8/2013 | Zhang et al. |
| 8,532,785 B1 | 9/2013 | Crutchfield |
| 8,541,131 B2 | 9/2013 | Lund et al. |
| 8,617,082 B2 | 12/2013 | Zhang et al. |
| 8,639,333 B2 | 1/2014 | Stadler et al. |
| 8,676,314 B2 | 3/2014 | Maskara et al. |
| 8,718,773 B2 | 5/2014 | Willis et al. |
| 8,744,572 B1 | 6/2014 | Greenhut et al. |
| 8,768,459 B2 | 7/2014 | Ghosh et al. |
| 8,886,307 B2 | 11/2014 | Sambelashvili et al. |
| 8,886,311 B2 | 11/2014 | Anderson et al. |
| 8,923,963 B2 | 12/2014 | Bonner et al. |
| 9,008,776 B2 | 4/2015 | Cowan et al. |
| 9,717,923 B2 | 8/2017 | Thompson-Nauman et al. |
| 9,789,319 B2 | 10/2017 | Sambelashvili |
| 9,808,633 B2 | 11/2017 | Bonner et al. |
| 2004/0215308 A1 | 10/2004 | Bardy et al. |
| 2005/0038477 A1 | 2/2005 | Kramer et al. |
| 2005/0137629 A1 | 6/2005 | Dyjach et al. |
| 2005/0277990 A1 | 12/2005 | Ostroff et al. |
| 2006/0161205 A1 | 7/2006 | Mitrani et al. |
| 2006/0235478 A1 | 10/2006 | Van Gelder et al. |
| 2006/0241705 A1 | 10/2006 | Neumann et al. |
| 2007/0049975 A1 | 3/2007 | Cates et al. |
| 2007/0088394 A1 | 4/2007 | Jacobson |
| 2007/0088398 A1 | 4/2007 | Jacobson |
| 2007/0293900 A1 | 12/2007 | Sheldon et al. |
| 2007/0299475 A1 | 12/2007 | Levin et al. |
| 2008/0154322 A1 | 6/2008 | Jackson et al. |
| 2008/0269816 A1 | 10/2008 | Prakash et al. |
| 2008/0269823 A1 | 10/2008 | Burnes et al. |
| 2009/0036941 A1 | 2/2009 | Corbucci |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0275998 A1 | 11/2009 | Burnes et al. |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0042108 A1 | 2/2010 | Hibino |
| 2010/0152798 A1 | 6/2010 | Sanghera et al. |
| 2010/0185250 A1 | 7/2010 | Rom |
| 2010/0198291 A1 | 8/2010 | Sambelashvili et al. |
| 2010/0228308 A1 | 9/2010 | Cowan et al. |
| 2010/0286541 A1 | 11/2010 | Musley et al. |
| 2011/0071586 A1 | 3/2011 | Jacobson |
| 2011/0106202 A1 | 5/2011 | Ding et al. |
| 2011/0190841 A1 | 8/2011 | Sambelashvili et al. |
| 2011/0196444 A1 | 8/2011 | Prakash et al. |
| 2012/0035685 A1 | 2/2012 | Saha et al. |
| 2012/0109235 A1 | 5/2012 | Sheldon et al. |
| 2012/0109236 A1 | 5/2012 | Jacobson et al. |
| 2012/0172892 A1 | 7/2012 | Grubec et al. |
| 2012/0263218 A1 | 10/2012 | Dal Molin et al. |
| 2012/0296228 A1 | 11/2012 | Zhang et al. |
| 2012/0316613 A1 | 12/2012 | Keefe et al. |
| 2013/0013017 A1 | 1/2013 | Mullen et al. |
| 2013/0053906 A1 | 2/2013 | Ghosh et al. |
| 2013/0066169 A1 | 3/2013 | Rys et al. |
| 2013/0116738 A1 | 5/2013 | Samade et al. |
| 2013/0131750 A1 | 5/2013 | Stadler et al. |
| 2013/0131751 A1 | 5/2013 | Stadler et al. |
| 2013/0197599 A1 | 8/2013 | Sambelashvili et al. |
| 2013/0231710 A1 | 9/2013 | Jacobson |
| 2013/0268017 A1 | 10/2013 | Zhang et al. |
| 2013/0274828 A1 | 10/2013 | Willis |
| 2013/0282073 A1 | 10/2013 | Cowan et al. |
| 2014/0114372 A1 | 4/2014 | Ghosh et al. |
| 2014/0121720 A1 | 5/2014 | Bonner et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0358135 A1 | 12/2014 | Sambelashvili et al. |
| 2015/0142070 A1 | 5/2015 | Sambelashvili |
| 2015/0306375 A1 | 10/2015 | Marshall et al. |
| 2015/0306410 A1 | 10/2015 | Marshall et al. |
| 2016/0051821 A1 | 2/2016 | Sambelashvili et al. |
| 2016/0114169 A1 | 4/2016 | Demmer et al. |

(56) References Cited

U.S. PATENT DOCUMENTS

| | | |
|---|---|---|
| 2016/0158567 A1 | 6/2016 | Marshall et al. |
| 2017/0014629 A1 | 1/2017 | Ghosh et al. |
| 2017/0028203 A1 | 2/2017 | Ghosh |
| 2017/0157395 A1 | 6/2017 | Thompson-Nauman et al. |
| 2017/0157399 A1 | 6/2017 | Anderson et al. |
| 2017/0157413 A1 | 6/2017 | Anderson et al. |
| 2017/0157414 A1 | 6/2017 | Anderson et al. |
| 2017/0274213 A1 | 9/2017 | Ghosh et al. |
| 2018/0028814 A1 | 2/2018 | Ghosh |

FOREIGN PATENT DOCUMENTS

| | | |
|---|---|---|
| EP | 2471452 A1 | 7/2012 |
| EP | 1703944 B1 | 7/2015 |
| EP | 3171936 A1 | 5/2017 |

OTHER PUBLICATIONS (PCT/US2014/013601) PCT Notification of Transmittal of the International Search Report and the Written Opinion of the International Searching Authority.

(PCT/US2014/036782) PCT Notification of Transmittal of the International Search Report and the Written Opinion of the International Searching Authority, dated Aug. 22, 2014, 12 pages.

"Epicardial Wireless Pacemaker for Improved Left Ventricular Resynchronization (Conceptual Design)" by Rodney Hawkins, Dec. 2010, Thesis presented to the Faculty of California Polytechnic State University, San Luis Obispo., 57 pp.

Ganapathy et al., "Implantable Device to Monitor Cardiac Activity with Sternal Wires," Pace, vol. 37, Dec. 2014, 11 pages.

Guenther et al., "Substernal Lead Implantation: A Novel Option to Manage DFT Failure in S-ICD patients," Clinical Research Cardiology, Published On-line Oct. 2, 2014, 3 pages.

McKenzie et al., "Single-Chamber Left-Ventricular vs. Dual-Chamber Right-Ventricular Pacing in CRT Patients: Insights Into Relative Importance of Atrio-Ventricular Versus Interventricular Synchrony and Implications for Leadless Pacing," Abstract of Moderated Poster, Heart Rhythm Society Annual Meeting, Boston, MA, 2015, S539.

Tung et al., "Initial Experience of Minimal Invasive Extra Cardiac Placement of High Voltage Defibrillator Leads," Canadian Cardiovascular Congress 2007, Oct. 2007, vol. 23, Supplement SC, Abstract 0697, http://www.pulsus.comccc2007/abs/0697.htm, 2 pages.

(PCT/US2019/025596) PCT Notification of Transmittal of the International Search Report and the Written Opinion of the International Searching Authority, dated Jul. 31, 2019, 11 pages.

FEATURE BASED SENSING FOR LEADLESS PACING THERAPY

The disclosure herein relates to delivery of a pacing therapy from a leadless cardiac pacing device system, and particularly to systems and methods for evaluation and adjustment of delivery of a pacing therapy delivered by a leadless cardiac pacing device.

BACKGROUND

During normal conduction of a human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers causing a depolarization and the resulting atrial chamber contractions. The excitation pulse is further transmitted to and through the ventricles via the atrioventricular (AV) node and a ventricular conduction system causing a depolarization and the resulting ventricular chamber contractions.

Disruption of this natural pacemaker and conduction system as a result of aging or disease can be treated by artificial cardiac pacing. For example, one or more heart chambers may be electrically paced depending on the location and severity of the conduction disorder. Cardiac therapy, such as cardiac resynchronization therapy (CRT), may correct symptoms of electrical dyssynchrony of a patient's heart by providing pacing therapy to one or both ventricles or atria, e.g., by providing pacing to encourage earlier activation of the left or right ventricles. By pacing the ventricles, the ventricles may be controlled such that they contract in synchrony.

Cardiac resynchronization devices operate by either delivering pacing stimulus to both ventricles or to one ventricle in synchrony with atrial activation, namely atrioventricular AV synchronous pacing, where ventricular pacing is delivered at a predetermined time interval following each atrial depolarization event at heart rates that are determined to be normal for atrioventricular tracking. The desired result of such pacing stimulus is a more or less simultaneous mechanical contraction and ejection of blood from the ventricles, and in synchrony with atrial contraction, thereby maintaining the AV synchrony and improving heart function. Ideally, each pacing pulse stimulus delivered to a ventricle evokes a response from the ventricle. Delivering electrical stimuli that causes the ventricle to respond is commonly referred to as capturing a ventricle.

Current implantable pacemakers and implantable cardioverter defibrillators (ICDs) are available for delivering electrical stimulation therapies to a patient's heart, such as cardiac resynchronization therapy (CRT). Medical device technology advancement has led toward smaller and smaller implantable devices. Recently, this reduction in size has resulted in the introduction of leadless intracardiac pacemakers that can be implanted directly in a heart chamber. An example of delivering cardiac resynchronization therapy using a subcutaneous device and a leadless pacing device pacing is described, for example, in U.S. Pat. No. 9,789,319, incorporated herein by reference in it's entirety. Timing of the delivery of a pacing therapy is an important consideration for ensuring effective capture during delivery of the pacing therapy by the leadless pacing device, and therefore improvements in effectively sensing and identifying specific desired features of a cardiac signal for timing delivery of a pacing therapy are needed.

SUMMARY

The exemplary system, device and methods described herein involve a cardiac pacing system and method for delivering a pacing therapy to a patient. For example, a cardiac pacing device system may include a substernal or subcutaneous device positioned extravascularly within the patient and a leadless pacing device positioned in the left ventricle, the right ventricle or both the left ventricle and the right ventricle of the patient. The substernal or subcutaneous device senses an atrial activation from far-field vectors, determine desired features or portions of the cardiac signal, and triggers delivery of the pacing therapy by the leadless pacing device based on the determined portion of the signal having the desired signal feature. One of the signal features may be a portion of the signal in which an atrial activation, or P-wave is determined to occur. Since an atrial activation, or P-wave, has a much lower signal amplitude relative to other cardiac signal components of a cardiac cycle, such as QRS and T-wave components, far-field sensing of the atrial activation via substernal or subcutaneous positioned sensing electrodes may be problematic.

Therefore, the present disclosure describes a cardiac pacing system and method that includes sensing an atrial activation from substernal or subcutaenous ECG signals. The method includes tracking features of a cardiac signal as sensing of a cardiac signal for a given cardiac cycle occurs. Features of the cardiac signal are determined within a certain time-window scanning across the signal in real-time. For example, differences may be determined between a maximum amplitude (Vmax) of the cardiac signal within the time-window, and an amplitude of the signal at the start (Vs) and end of the window (Ve). In another example, differences may be determined between a minimum amplitude (Vmin) of the cardiac signal within the time-window and an amplitude of the signal at the start (Vs) and end of the window (Ve). If one or more of the features do not meet a predetermined threshold, the time-window is advanced across the sensed cardiac signal for the same sensed cardiac cycle, and the process is repeated. On the other hand, if one or more of the features meet the predetermined threshold, an atrial event is determined to be sensed and a triggering signal may be transmitted from the substernal or subcutaneous to the leadless pacemaker in the ventricle, instructing the leadless pacemaker to pace at a predetermined time following the sensed atrial event.

In one example, a method of delivering a cardiac pacing therapy comprises sensing a cardiac signal; determining signal characteristics of the cardiac signal within a signal evaluation window positioned along a first portion of a cardiac cycle; determining whether a P-wave occurs within the signal evaluation window associated with the first portion of the cardiac cycle in response to the determined signal characteristics; adjusting the signal evaluation window to be positioned along a second portion of the cardiac cycle in response to the P-wave not occurring within the signal evaluation window; determining signal characteristics of the cardiac signal within the signal evaluation window positioned along the second portion of the cardiac cycle; determining whether a P-wave occurs in response to the signal characteristics determined within the signal evaluation window positioned along the second portion of the cardiac cycle; and delivering ventricular pacing therapy in response to a P-wave being determined to occur.

In another example, a cardiac pacing system for delivering a cardiac pacing therapy, comprises: an implantable cardioverter defibrillator (ICD), the ICD comprising a housing; a lead having a lead body and electrically coupled to the housing of the ICD; a plurality of electrodes positioned along the lead body; a control circuit positioned within the housing of the ICD and configured to determine a cardiac signal sensed between two electrodes of the plurality of electrodes positioned along the lead body or between the housing of the ICD and an electrode of the plurality of electrodes positioned along the lead body, determine signal characteristics of the cardiac signal within a signal evaluation window positioned along a first portion of a cardiac cycle, determine whether a P-wave occurs within the signal evaluation window associated with the first portion of the cardiac cycle in response to the determined signal characteristics, adjust the signal evaluation window to be positioned along a second portion of the cardiac cycle in response to the P-wave not occurring within the signal evaluation window, determine signal characteristics of the cardiac signal within the signal evaluation window positioned along the second portion of the cardiac cycle, determine whether a P-wave occurs in response to the signal characteristics determined within the signal evaluation window positioned along the second portion of the cardiac cycle, and deliver a trigger signal in response to a P-wave being determined to occur; a leadless pacing device comprising a housing; a plurality of electrodes positioned along the housing of the leadless pacing device; and a control circuit positioned within the housing of the leadless pacing device and configured to receive the trigger signal from the ICD and deliver a ventricular pacing therapy via the plurality of electrodes positioned along the housing of the leadless pacing device.

In another example, a non-transitory computer readable medium storing instructions which cause a cardiac pacing device system to perform a method comprises: sensing a cardiac signal; determining signal characteristics of the cardiac signal within a signal evaluation window positioned along a first portion of a cardiac cycle; determining whether a P-wave occurs within the signal evaluation window associated with the first portion of the cardiac cycle in response to the determined signal characteristics; adjusting the signal evaluation window to be positioned along a second portion of the cardiac cycle in response to the P-wave not occurring within the signal evaluation window; determining signal characteristics of the cardiac signal within the signal evaluation window positioned along the second portion of the cardiac cycle; determining whether a P-wave occurs in response to the signal characteristics determined within the signal evaluation window positioned along the second portion of the cardiac cycle; and delivering ventricular pacing therapy in response to a P-wave being determined to occur.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
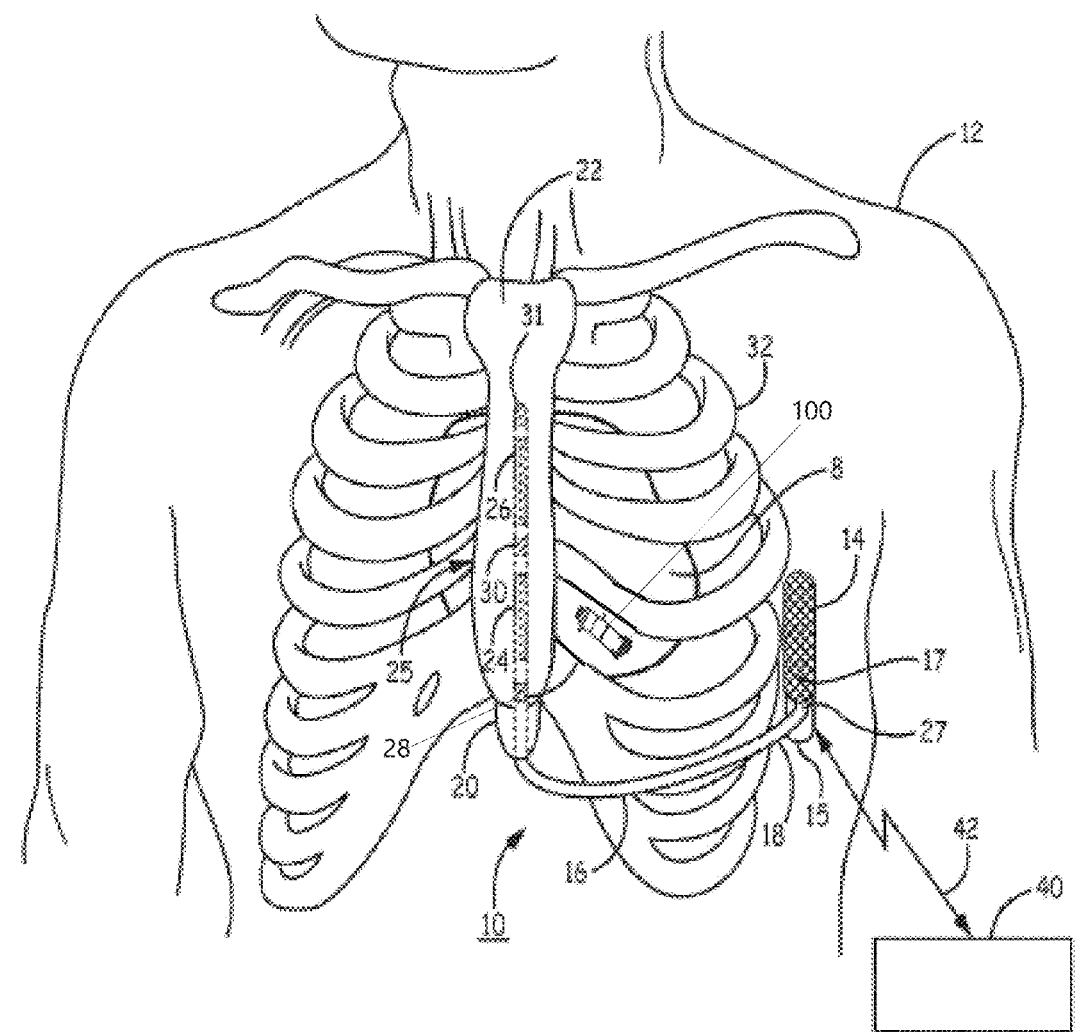
FIG. 1 is a schematic diagram of a leadless cardiac pacing system, according to an example of the present disclosure.

In the following detailed description of illustrative embodiments, reference is made to the accompanying figures of the drawing which form a part hereof, and in which are shown, by way of illustration, specific embodiments which may be practiced. It is to be understood that other embodiments may be utilized, and structural changes may be made without departing from (e.g., still falling within) the scope of the disclosure presented hereby.

Exemplary systems and methods shall be described with reference to FIGS. 1-7. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The exemplary system, device and methods described herein involve a cardiac pacing system and method for delivering a pacing therapy to a patient. For example, a cardiac pacing device system may include a substernal or subcutaneous device positioned extravascularly within the patient and a leadless pacing device positioned in the left ventricle, the right ventricle or both the left ventricle and the right ventricle of the patient. The substernal or subcutaneous device senses an atrial activation from far-field vectors, determine desired features or portions of the cardiac signal, and triggers delivery of the pacing therapy by the leadless pacing device based on the determined portion of the signal having the desired signal feature. One of the signal features may be a portion of the signal in which an atrial activation, or P-wave is determined to occur. Since an atrial activation, or P-wave, has a much lower signal amplitude relative to other cardiac signal components of a cardiac cycle, such as QRS and T-wave components, far-field sensing of the atrial activation via substernal or subcutaneous positioned sensing electrodes may be problematic.

Therefore, the present disclosure describes a cardiac pacing system and method that includes sensing an atrial activation from substernal or subcutaenous ECG signals. The method includes tracking features of a cardiac signal as sensing of a cardiac signal for a given cardiac cycle occurs. Features of the cardiac signal are determined within a certain time-window scanning across the signal in real-time. For example, differences may be determined between a maximum amplitude (Vmax) of the cardiac signal within the time-window, and an amplitude of the signal at the start (Vs) and end of the window (Ve). In another example, differences may be determined between a minimum amplitude (Vmin) of the cardiac signal within the time-window and an amplitude of the signal at the start (Vs) and end of the window (Ve). If one or more of the features do not meet a predetermined threshold, the time-window is advanced across the sensed cardiac signal for the same sensed cardiac cycle, and the process is repeated. On the other hand, if one or more of the features meet the predetermined threshold, an atrial event is determined to be sensed and a triggering signal may be transmitted from the substernal or subcutaneous to the leadless pacemaker in the ventricle, instructing the leadless pacemaker to pace at a predetermined time following the sensed atrial event.

FIG. 1 is a schematic diagram of a leadless cardiac pacing system, according to an example of the present disclosure. As illustrated in FIG. 1, a leadless cardiac pacing system 10 may include an implantable cardioverter defibrillator (IC) 14 that includes a housing 15 that forms a hermetic seal that protects internal components of ICD 14, along with a leadless cardiac pacing device 100 shown positioned in the right ventricle of a patient 12. The housing 15 of ICD 14 may be formed of a conductive material, such as titanium or titanium alloy. The housing 15 may function as an electrode (sometimes referred to as a can electrode). Housing 15 may be used as an active can electrode for use in delivering cardioversion/defibrillation (CV/DF) shocks or other high voltage pulses delivered using a high voltage therapy circuit. In other examples, housing 15 may be available for use in delivering unipolar, low voltage cardiac pacing pulses in conjunction with lead-based cathode electrodes and for sensing cardiac electrical signals including far-field atrial events in conjunction with lead-based electrodes. In other instances, the housing 15 of ICD 14 may include a plurality of electrodes on an outer portion of the housing. The outer portion(s) of the housing 15 functioning as an electrode(s) may be coated with a material, such as titanium nitride.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, electrical cardiac signal sensing circuitry, therapy delivery circuitry, power sources and other components for sensing cardiac electrical signals, detecting a heart rhythm, and controlling and delivering electrical stimulation pulses to treat an abnormal heart rhythm.

Lead 16 includes an elongated lead body 18 having a proximal end 27 that includes a lead connector (not shown) configured to be connected to ICD connector assembly 17 and a distal portion 25 that includes one or more electrodes. In the example illustrated in FIG. 1, the distal portion 25 of lead 16 includes defibrillation electrodes 24 and 26 and pace/sense electrodes 28, 30 and 31. In some instances, defibrillation electrodes 24 and 26 are coupled to electrically isolated conductors, and ICD 14 may include switching mechanisms to allow electrodes 24 and 26 to be utilized as a single defibrillation electrode (e.g., activated concurrently to form a common cathode or anode) or as separate defibrillation electrodes, (e.g., activated individually, one as a cathode and one as an anode or activated one at a time, one as an anode or cathode and the other remaining inactive with housing 15 as an active electrode).

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to low voltage pacing and sensing electrodes 28, 30 and 31. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, electrodes 24 and 26 may be used in a pacing electrode vector for delivering extra-cardiovascular pacing pulses, such as ventricular pacing pulses in an atrial tracking or non-tracking pacing mode, and/or in a sensing vector used to sense cardiac electrical signals including far-field atrial events for controlling ventricular pacing and for detecting ventricular tachyarrhythmias for controlling high voltage therapies.

Electrodes 28, 30 and 31 are relatively smaller surface area electrodes for delivering low voltage pacing pulses and for sensing cardiac electrical signals. Electrodes 28, 30 and 31 are referred to as pace/sense electrodes because they are generally configured for use in low voltage applications, e.g., used as either a cathode or anode for delivery of pacing pulses and/or sensing of cardiac electrical signals. In some instances, electrodes 28, 30 and 31 may provide only pacing functionality, only sensing functionality or both.

Electrode 28 is shown proximal to defibrillation electrode 24, and electrode 30 is located between defibrillation electrodes 24 and 26. A third pace/sense electrode 31 may be located distal to defibrillation electrode 26. Electrodes 28 and 30 are illustrated as ring electrodes, and electrode 31 is illustrated as a hemispherical tip electrode in the example of FIG. 1. However, electrodes 28, 30 and 31 may comprise any of a number of different types of electrodes, including ring electrodes, short coil electrodes, hemispherical electrodes, directional electrodes, segmented electrodes, or the like, and may be positioned at any position along the distal portion 25 of lead 16 and are not limited to the positions shown. Further, electrodes 28, 30 and 31 may be of similar type, shape, size and material or may differ from each other.

Lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly beneath sternum 22. Extra-cardiovascular lead 16 of system 10 is implanted at least partially underneath sternum 22 of patient 12. At a location near xiphoid process 20, lead 16 may bend or turn and extend superiorly within the anterior mediastinum in a substernal position. A lead implanted such that the distal portion 25 is substantially within anterior mediastinum may be referred to as a "substernal lead."

In the example illustrated in FIG. 1, lead 16 is located substantially centered under sternum 22. In other instances, however, lead 16 may be implanted such that it is offset laterally from the center of sternum 22. Lead 16 may angle laterally such that distal portion 25 of lead 16 is underneath/ below the ribcage 32 in addition to or instead of sternum 22. The distal portion 25 of lead 16 may be offset laterally from sternum 22, e.g., to the right or left of sternum 22, angled laterally from sternum 22 toward the left or the right, or the like. In other examples, the distal portion 25 of lead 16 may be implanted in other extra-cardiovascular, intra-thoracic locations, including the pleural cavity or around the perimeter of and adjacent to but typically not within the pericardium 38 of heart 8.

Electrical conductors (not illustrated) extend through one or more lumens of the elongated lead body 18 of lead 16 from the lead connector at the proximal lead end 27 to respective electrodes 24, 26, 28, 30 and 31 located along the distal portion 25 of the lead body 18. The lead body 18 of lead 16 may be formed from a non-conductive material, including silicone, polyurethane, fluoropolymers, mixtures thereof, and other appropriate materials, and shaped to form one or more lumens within which the one or more conductors extend. However, the techniques disclosed herein are not limited to such constructions or to any particular lead body design.

The respective conductors electrically couple the electrodes 24, 26, 28, 30 and 31 to circuitry, such as a therapy delivery circuit and/or a sensing circuit as described below, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28, 30 and 31 and transmit sensed electrical signals from one or more of defibrillation electrodes 24 and 26 and/or pace/sense electrodes 28, 30 and 31 to the sensing circuit within ICD 14.

ICD 14 may obtain electrical signals corresponding to electrical activity of heart 8 via a combination of sensing vectors that include combinations of electrodes 28, 30, and/or 31. In some examples, housing 15 of ICD 14 is used in combination with one or more of electrodes 28, 30 and/or 31 in a sensing electrode vector. ICD 14 may even obtain cardiac electrical signals using a sensing vector that includes one or both defibrillation electrodes 24 and/or 26, e.g., between electrodes 24 and 26 or one of electrodes 24 or 26 in combination with one or more of electrodes 28, 30, 31, and/or the housing 15.

ICD 14 analyzes the cardiac electrical signals received from one or more of the sensing vectors to monitor for abnormal rhythms, such as bradycardia, ventricular tachycardia (VT) or ventricular fibrillation (VF). ICD 14 may analyze the heart rate and/or morphology of the cardiac electrical signals to monitor for tachyarrhythmia in accordance with any of a number of tachyarrhythmia detection techniques. One example technique for detecting tachyarrhythmia is described in U.S. Pat. No. 7,761,150 (Ghanem, et al.), incorporated by reference herein in its entirety.

ICD 14 generates and delivers electrical stimulation therapy in response to detecting bradycardia or a tachyarrhythmia (e.g., VT or VF). ICD 14 may deliver anti-tachycardia pacing (ATP) in response to VT detection, and in some cases may deliver ATP prior to a cardioversion/ defibrillation (CV/DF) shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15.

Ventricular pacing pulses may be delivered using an extra-cardiovascular pacing electrode vector selected from any of electrodes 24, 26, 28, 30, 31 and/or housing 15. Ventricular pacing mode may be controlled based on far-field atrial events sensed using a sensing vector selected from electrodes 24, 26, 28, 30 31 and/or housing 15. The pacing electrode vector may be different than the sensing electrode vector. In one example, cardiac electrical signals are sensed between pace/sense electrodes 28 and 30 and/or between one of pace/sense electrodes 28 or 30 and housing 15, and pacing pulses are delivered between pace/sense electrode 30 used as a cathode electrode and defibrillation electrode 24 used as a return anode electrode. In other examples, pacing pulses may be delivered between pace/ sense electrode 28 and either (or both) defibrillation electrodes 24 or 26 or between defibrillation electrode 24 and defibrillation electrode 26. These examples are not intended to be limiting, and it is recognized that other sensing electrode vectors and pacing electrode vectors may be selected according to individual patient need. The techniques for controlling pacing mode switching are not limited by pacing electrode vector and electrode positions. Various examples of extra-cardiovascular IMD systems and associated techniques for delivering extra-cardiovascular pacing pulses are described in U.S. patent application Ser. No. 14/957,651 (Thompson-Nauman, et al.), U.S. patent application Ser. Nos. 15/367,516 and 15/367,777 (Anderson, et al.) and U.S. patent application Ser. No. 15/368,197 (Anderson, et al.), all of which are incorporated herein by reference in their entirety.

FIG. 1 is illustrative in nature and should not be considered limiting of the practice of the techniques in an extra-cardiovascular ICD system as disclosed herein. In other examples, extra-cardiovascular lead 16 may include more or fewer electrodes than the number of electrodes shown in FIG. 1, and the electrodes may be arranged along the lead 16 in different configurations than the particular arrangement shown in FIG. 1. Various example configurations of extra-cardiovascular leads and electrodes and dimensions that may be implemented in conjunction with the extra-cardiovascular pacing techniques disclosed herein are described in U.S. Publication No. 2015/0306375 (Marshall, et al.) and U.S. Publication No. 2015/0306410 (Marshall, et al.), both of which are incorporated herein by reference in their entirety. Other examples of extra-cardiovascular leads including one or more defibrillation electrodes and one or more pacing and sensing electrodes carried by curving, serpentine, undulating or zig-zagging distal portion of the lead body that may be implemented with the pacing techniques described herein are generally disclosed in U.S. Pat. Publication No. 2016/ 0158567, (Marshall, et al.), incorporated herein by reference in its entirety.

In other examples, the distal portion 25 may extend subcutaneously or submuscularly over the ribcage and/or sternum or along other subcutaneous or submuscular paths. For instance, the distal portion 25 of lead 16 may be implanted outside the thorax, over the sternum/ribcage rather than in the substernal space as shown in FIG. 1. The path of extra-cardiovascular lead 16 may depend on the location of ICD 14, the arrangement and position of electrodes carried by the lead distal portion 25, and/or other factors. For example, ICD 14 is shown implanted subcutaneously on the left side of patient 12 along the ribcage 32, but in other examples ICD 14 may be implanted between the left posterior axillary line and the left anterior axillary line of patient 12 or other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally.

An external device 40 may be used to establish a telemetric communication link 42 with ICD 14 to retrieve data from ICD 14 and to program operating parameters and algorithms in ICD 14 for controlling ICD functions. Data stored or acquired by ICD 14, including physiological signals or associated data derived therefrom, results of device diagnostics, and histories of detected rhythm episodes and delivered therapies, may be retrieved from ICD 14 by external device 40 following an interrogation command. External device 40 may alternatively be embodied as a home monitor or handheld device.

External device 40 is often referred to as a "programmer" because it is typically used by a physician, technician, nurse, clinician or other qualified user for programming operating parameters in pacemaker 100 and ICD 14 as well as for retrieving device- and/or patient-related data from pacemaker 100 and ICD. External device 40 may be located in a clinic, hospital or other medical facility. External device 40 may alternatively be embodied as a home monitor or a handheld device that may be used in a medical facility, in the patient's home, or another location. Operating parameters, such as sensing and therapy delivery control parameters, may be programmed into pacemaker 100 using external device 40.

External device 40 may include a microprocessor, memory, user display, user interface (such as a mouse, keyboard, or pointing device) and telemetry circuit for receiving, transmitting and processing signals sent to or received from pacemaker 100 and for enabling a clinician to view data and enter programming commands. Aspects of external device 40 may generally correspond to the external programming/monitoring unit disclosed in U.S. Pat. No. 5,507,782 (Kieval, et al.), incorporated herein by reference in its entirety.

Pacemaker 100 may be a transcatheter intracardiac pacemaker adapted for implantation within the heart, e.g., within the right ventricle (RV) or within the left ventricle (LV), for sensing cardiac signals and delivering cardiac pacing pulses to the respective ventricle in which pacemaker 100 is implanted. Pacemaker 100 is shown positioned along an endocardial wall of the left ventricle, e.g., near the left ventricular apex. The techniques disclosed herein, however, are not limited to the pacemaker location shown in the example of FIG. 1 and other relative locations within or along the right or left ventricular chamber for delivering ventricular pacing pulses are possible.

Pacemaker 100 is capable of producing electrical stimulation pulses, e.g., pacing pulses, delivered to a patient's heart 8 via one or more electrodes on the outer housing of the pacemaker 100. Pacemaker 100 is may be configured to sense a cardiac electrical signal using the housing-based electrodes. The cardiac electrical signal may include far-field atrial events, e.g., P-waves occurring in the right atrium (RA).

Figure 2:
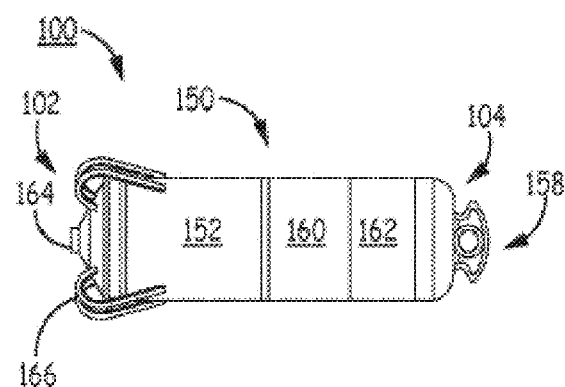
FIG. 2 is a schematic diagram of a leadless pacing device of a leadless cardiac pacing system, according to an example of the present disclosure.

FIG. 2 is a schematic diagram of a leadless pacing device of a leadless cardiac pacing system, according to an example of the present disclosure. As illustrated in FIG. 2, leadless pacing device 100 may include two housing-based electrodes 162 and 164 spaced apart along the housing 150 for sensing cardiac electrical signals and delivering pacing pulses. Electrode 164 is shown as a tip electrode along a distal end 102 of pacemaker housing 150. Electrode 162 is shown as a ring electrode along a mid-portion of housing 150, for example adjacent housing proximal end 104. Housing distal end 102 is referred to as "distal" in that it is expected to be the leading end as it advanced to an implant site using a delivery tool, such as a catheter, and placed against a targeted pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 100 may include two or more ring electrodes, two tip electrodes, and/or other types of electrodes exposed along pacemaker housing 150 for delivering electrical stimulation to heart 8 and sensing cardiac electrical signals that include near-field ventricular events, e.g., R-waves attendant to ventricular depolarizations, and far-field atrial events, e.g., P-waves attendant to atrial depolarizations. Electrodes 162 and 164 may be, without limitation, titanium, platinum, iridium or alloys thereof and may include a low polarizing coating, such as titanium nitride, iridium oxide, ruthenium oxide, platinum black among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150, isolated from cathode tip electrode 164, may function as an electrode instead of providing a localized electrode, such as electrode 162, to serve as a return anode electrode for delivering bipolar pacing and sensing.

The housing 150 includes a control electronics subassembly 152, which houses the electronic circuitry for sensing cardiac signals, producing pacing pulses and controlling ventricular pacing pulse delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae or actively engaging endocardial tissue. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), hereby incorporated herein by reference in its entirety.

In some examples, pacemaker 100 may include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

Figure 3:
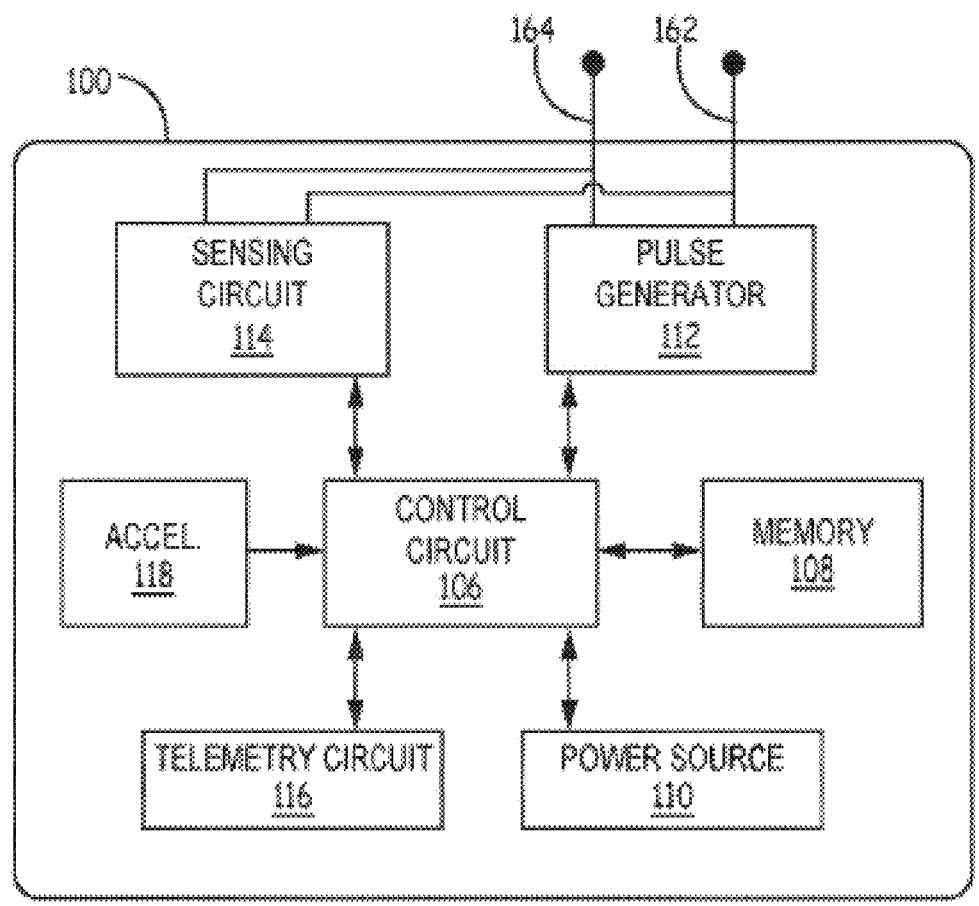
FIG. 3 is a functional block diagram of an example leadless pacing device of a leadless cardiac pacing system, according to an example of the present disclosure.

FIG. 3 is a functional block diagram of an example leadless pacing device of a leadless cardiac pacing system, according to an example of the present disclosure. As illustrated in FIG. 3, leadless pacing device 100 may include a control circuit 106, memory 108, power source 110, pulse generator 112, sensing circuit 114 and telemetry circuit 116. Electrodes 162 and 164 are shown coupled to pulse generator 112 and sensing circuit 114 to provide bipolar cardiac electrical signal sensing and pacing pulse delivery. A pulse generator 112 generates electrical stimulation pulses that are delivered to heart tissue via electrodes 162 and 164. Pulse generator 112 may include one or more holding capacitors and a charging circuit to charge the capacitor(s) to a pacing pulse voltage. At controlled time intervals, the holding capacitor(s) may be discharged through an output capacitor across a pacing load, e.g., across electrodes 162 and 164. Pacing circuitry generally disclosed in U.S. Pat. No. 8,532,785 (Crutchfield), hereby incorporated herein by reference in its entirety, may be implemented in pacemaker 100 for charging a pacing capacitor to a predetermined pacing pulse amplitude under the control of control circuit 106 and delivering a pacing pulse.

Control circuit 106 may include a pace timing circuit that includes one or more timers or counters set according to programmed pacing escape intervals, which may be stored in memory 108. A pacing escape interval may be set to a V-V interval during atrial-asynchronous ventricular pacing. An atrial-asynchronous ventricular pacing mode is a non-tracking pacing mode during which ventricular pacing pulses are delivered independent of the timing of atrial activity. The V-V interval may be started when sensing circuit 114 senses an R-wave or when pulse generator 112 delivers a ventricular pacing pulse. If sensing circuit 114 senses an R-wave from the cardiac electrical signal prior to the V-V interval expiring, the V-V interval is restarted and the scheduled pacing pulse is inhibited. If the V-V interval expires without the sensing circuit 114 sensing an R-wave, the scheduled pacing pulse is delivered by pulse generator 114.

At other times, control circuit 106 may control pulse generator 112 to deliver ventricular pacing pulses in an atrial-synchronized pacing mode. An atrial-synchronized pacing mode is an atrial-tracking mode during which the timing of ventricular pacing pulses is dependent on, e.g., triggered by, sensed far-field atrial events such as P-waves from an electrical signal or atrial mechanical systole, sometimes referred to as "atrial kick" sensed from a mechanical sensor such as a motion sensor. Ventricular pacing pulses track the atrial rate. In this case, the pace timing circuit of control circuit 106 may set a timer or counter to an A-V interval when the sensing circuit 114 senses an atrial P-wave. If an R-wave is not sensed by sensing circuit 114 during the A-V interval, a ventricular pacing pulse is delivered by pulse generator 112 at the expiration of the A-V interval, synchronizing ventricular electrical activation (and ventricular mechanical systole) to the timing of the atrial activity. If an R-wave is sensed during the A-V interval, the ventricular pacing pulse may be inhibited and a new A-V interval may be restarted upon sensing the next atrial P-wave by sensing circuit 114.

Sensing circuit 114 receives a cardiac electrical signal, e.g., across electrodes 162 and 164 and may include an analog filter and amplifier, an analog-to-digital converter, a digital filter, a rectifier, a sense amplifier, comparator or other event detection circuitry or components for filtering, amplifying and rectifying the cardiac electrical signal and for sensing cardiac electrical events such as far-field P-waves and near-field R-waves from the cardiac electrical signal.

Control circuit 106 may use the sensed event signals received from sensing circuit 114 in controlling the delivery of ventricular pacing pulses, e.g., by starting and restarting pacing escape intervals in response to sensed events and inhibiting pacing pulses. Control circuit 106 may determine PP intervals between consecutively sensed P-waves and/or other time intervals defined by sensed P-waves for use in automatically switching between atrial-synchronized and atrial-asynchronous ventricular pacing. Techniques for sensing P-waves by intracardiac pacemaker 100 may correspond to the methods disclosed in U.S. Pat. Publication No. 2016/0114169 A1 (Demmer, et al.), incorporated herein by reference in its entirety.

Sensing of far-field atrial activity for use in controlling ventricular pacing is not limited to sensing atrial electrical activity. In some examples, pacemaker 100 may include an accelerometer 118 or other motion sensor producing a signal correlated to patient and cardiac motion. The accelerometer signal includes far-field atrial mechanical event signals. Control circuit 106 may detect an atrial mechanical event, e.g., atrial systole or correlated to the timing of atrial systole, from a signal received from accelerometer 118. Atrial mechanical events may be used instead of or in combination with atrial electrical events for determining atrial event time intervals and controlling automatic switching from atrial-synchronized to atrial-asynchronous ventricular pacing based on the sensed atrial events and associated time intervals. An intracardiac pacemaker and associated techniques for detecting atrial events from a motion signal, e.g., from an accelerometer signal, are generally disclosed in U.S. patent application Ser. No. 15/140,585 (Ghosh, et al., filed Apr. 28, 2016), incorporated herein by reference in its entirety.

Control circuit 106 may be a microprocessor-based controller that communicates with memory 108, pulse generator 112, sensing circuit 114 and telemetry circuit 116, and accelerometer 118 for example via a data bus. Power source 110 provides power to each of the other components of pacemaker 100 as required. Control circuit 106 may execute power control operations to control when various components are powered to perform various pacemaker functions and when they are powered down to conserve energy. Power source 110 may include one or more energy storage devices, such as one or more rechargeable or non-rechargeable batteries. Power source 110 provides power to pulse generator for charging pacing capacitor(s) for generating pacing pulses.

Circuitry represented by the block diagram shown in FIG. 3 and other IMD block diagrams presented herein may include any discrete and/or integrated electronic circuit components that implement analog and/or digital circuits capable of producing the functions attributed to pacemaker 100 or another IMD performing the automatic ventricular pacing mode switching as described herein. The functions attributed to pacemaker 100 or other IMDs presented herein may be embodied as one or more processors, hardware, firmware, software, or any combination thereof. Control circuit 106 may include any one or more of a microprocessor, a controller, a digital signal processor (DSP), an application specific integrated circuit (ASIC), a field-programmable gate array (FPGA), state machine, or equivalent discrete or integrated logic circuitry.

Depiction of different features of leadless pacing device 100 as discrete circuits or components is intended to highlight different functional aspects and does not necessarily imply that such circuits must be realized by separate hardware or software components. Rather, functionality associated with one or more circuits may be performed by separate hardware or software components, or integrated within common or separate hardware or software components, which may include combinational or sequential logic circuits, state machines, memory devices, etc.

Memory 108 may include computer-readable instructions that, when executed by control circuit 106, cause control circuit 106 to perform various functions attributed throughout this disclosure to pacemaker 100. The computer-readable instructions may be encoded within memory 108. Memory 108 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal.

Leadless pacing device 100 includes a telemetry circuit 116 having a transceiver and antenna for bidirectional communication with external device 40 and for receiving a trigger signal from the ICD instructing the leadless pacing device 100 to delivery pacing therapy, as described below. Sensing control parameters and pacing control parameters may be received from external device 40 via telemetry circuit 116 and passed to control circuit 106 or stored in memory 108 for retrieval by control circuit 106 as needed.

Figure 4:
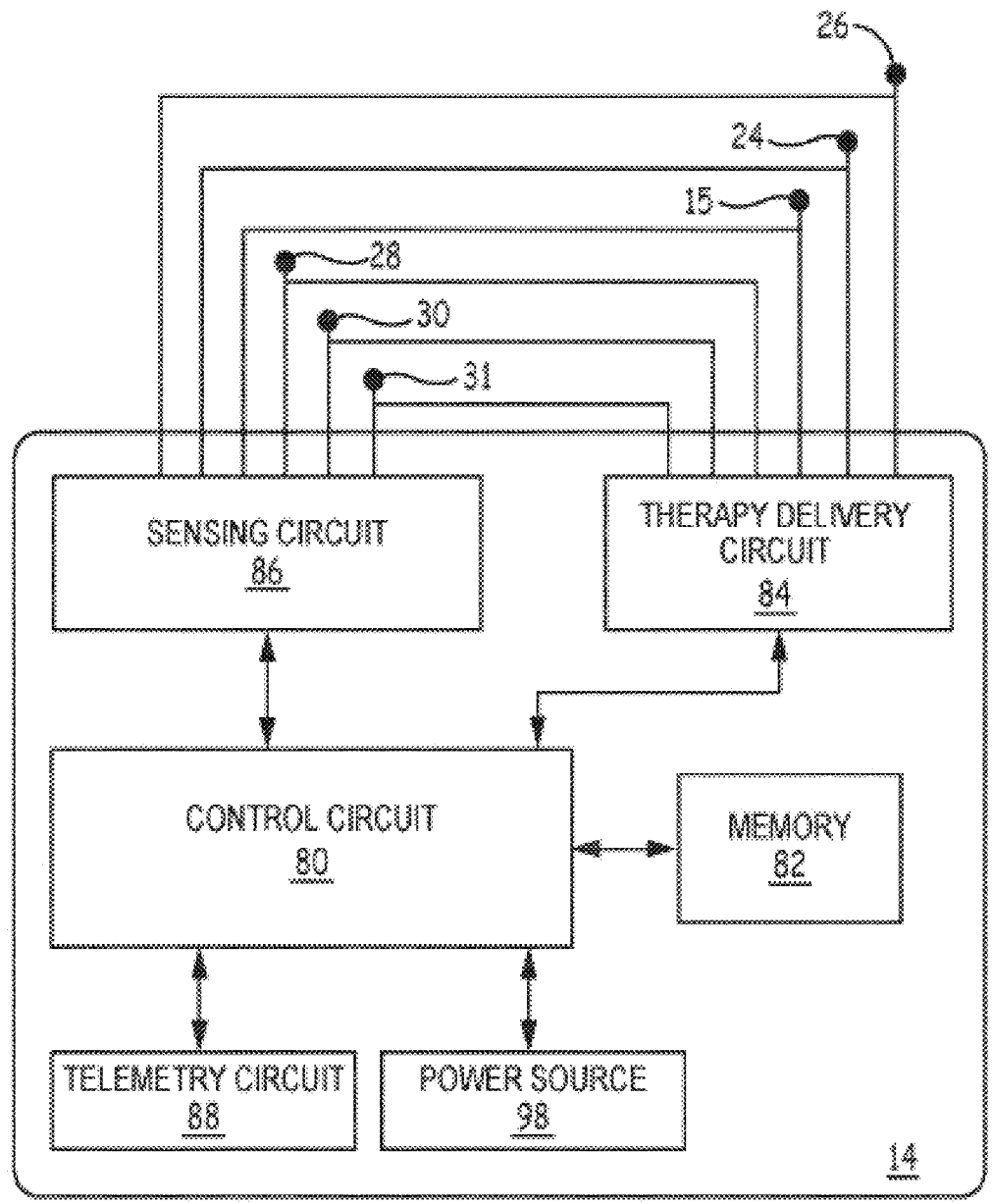
FIG. 4 is a functional block diagram of an example an extravascular cardioverter defibrillator of a leadless cardiac pacing system, according to an example of the present disclosure.

FIG. 4 is a functional block diagram of an example an extravascular cardioverter defibrillator of a leadless cardiac pacing system, according to an example of the present disclosure. As illustrated in FIG. 4, electronic circuitry enclosed within housing 15 (shown schematically as an electrode in FIG. 4) includes software, firmware and hardware that cooperatively monitor cardiac electrical signals, determine when an electrical stimulation therapy is necessary, and deliver therapies as needed according to programmed therapy delivery algorithms and control parameters. The software, firmware and hardware are configured to detect tachyarrhythmias and deliver anti-tachyarrhythmia therapy, e.g., detect ventricular tachyarrhythmias and in some cases discriminate VT and VF for determining when ATP or CV/DF shocks are required. According to the techniques disclosed herein, the software, firmware and hardware are further configured to sense far-field atrial events and control delivery of a cardiac pacing therapy by the leadless pacing device 100, as described below.

ICD 14 includes a control circuit 80, a memory 82, a therapy delivery circuit 84, a sensing circuit 86, and a telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 4 but are not shown for the sake of clarity. For example, power source 98 may be coupled to a low voltage (LV) charging circuit and to a high voltage (HV) charging circuit included in therapy delivery circuit 84 for charging low voltage and high voltage capacitors, respectively, included in therapy delivery circuit 84 for producing respective low voltage pacing pulses, such as cardiac resynchronization pacing, bradycardia pacing, post-shock pacing or ATP pulses, or for producing high voltage pulses, such as CV/DF shock pulses. In some examples, high voltage capacitors are charged and utilized for delivering pacing pulses, e.g., for ATP, post-shock pacing or other ventricular pacing pulses, instead of low voltage capacitors. Power source 98 is also coupled to components of sensing circuit 86, such as sense amplifiers, analog-to-digital converters, switching circuitry, etc. as needed.

The functional blocks shown in FIG. 4 represent functionality included in ICD 14 and may include any discrete and/or integrated electronic circuit components that implement analog and/or digital circuits capable of producing the functions attributed to ICD 14 herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern IMD system, given the disclosure herein, is within the abilities of one of skill in the art.

Memory 82 may include any volatile, non-volatile, magnetic, or electrical non-transitory computer readable storage media, such as a random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 or other ICD components to perform various functions attributed to ICD 14 or those ICD components. The non-transitory computer-readable media storing the instructions may include any of the media listed above.

The functions attributed to ICD 14 herein may be embodied as one or more integrated circuits. Depiction of different features as components is intended to highlight different functional aspects and does not necessarily imply that such components must be realized by separate hardware or software components. Rather, functionality associated with one or more components may be performed by separate hardware, firmware or software components, or integrated within common hardware, firmware or software components.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 and 31 and the housing 15, which may function as a common or ground electrode or as an active can electrode for delivering CV/DF shock pulses or cardiac pacing pulses.

Sensing circuit 86 may be selectively coupled to electrodes 28, 30, 31 and/or housing 15 in order to monitor electrical activity of the patient's heart. Sensing circuit 86 may additionally be selectively coupled to defibrillation electrodes 24 and/or 26 for use in a sensing electrode vector. Sensing circuit 86 may include multiple sensing channels for receiving cardiac electrical signals from two or more sensing electrode vectors selected from the available electrodes 24, 26, 28, 30, 31 and housing 15. For example, sensing circuit 86 may include a ventricular sensing channel configured to sense ventricular R-waves from a received cardiac electrical signal and an atrial sensing channel configured to sense far-field atrial P-waves from the same or a difference cardiac electrical signal. Sensing circuit 86 may include switching circuitry for selecting which of electrodes 24, 26, 28, 30, 31 and housing 15 are coupled to the one or more sensing channels. Switching circuitry may include a switch array, switch matrix, multiplexer, or any other type of switching device suitable to selectively couple components of sensing circuit 86 to selected electrodes.

Cardiac event detection circuitry within sensing circuit 86 may include one or more sense amplifiers, filters, rectifiers, threshold detectors, comparators, analog-to-digital converters (ADCs), or other analog or digital components configured to filter and amplify a cardiac electrical signal received from a selected sensing electrode vector and sense cardiac events, e.g., P-waves and R-waves. A cardiac event sensing threshold may be automatically adjusted by sensing circuit 86 under the control of control circuit 80, based on timing intervals and sensing threshold values determined by control circuit 80, stored in memory 82, and/or controlled by hardware of control circuit 80 and/or sensing circuit 86.

Control circuit 80 may include a pacer timing and control module, which may be embodied as hardware, firmware, software, or any combination thereof. The pacer timing and control module may include one or more dedicated hardware circuits, such as an ASIC, separate from the control circuit 80, such as a microprocessor, and/or a software module executed by a component of control circuit 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period and provide signals from sensing module 86 to blank one or more channels, e.g., amplifiers, for a period during and after delivery of electrical stimulation to the heart 8. The durations of these intervals may be determined in response to stored data in memory 82. The pacer timing and control module of the control module may also determine the amplitude of the cardiac pacing pulses.

During pacing, escape interval counters within the pacer timing/control module may be reset upon sensing of R-waves and P-waves. The timing and control module may reset the escape interval counters upon the generation of pacing pulses, and thereby control the basic timing of cardiac pacing functions, including anti-tachyarrhythmia pacing.

In some examples, the timing and control module may operate as an interrupt driven device and may be responsive to interrupts from pacer timing and control module, where the interrupts may correspond to the occurrences of sensed P-waves and R-waves and the generation of cardiac pacing pulses. Any necessary mathematical calculations may be performed by the control circuit 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the control 80 in response to the occurrence of a pace or sense interrupt to determine whether the patient's heart 8 is presently exhibiting atrial or ventricular tachyarrhythmia.

Upon detecting a cardiac event based on a sensing threshold crossing, sensing circuit 86 may produce a sensed event signal, such as a P-wave sensed event signal or an R-wave sensed event signal, which is passed to control circuit 80. Sensing circuit 86 may be configured to sense a far-field cardiac signal, determine desired features of the sensed cardiac signal and if certain feature thresholds of the signal are satisfied, transmit a trigger signal to the leadless pacing device 100 instructing the leadless pacing device 100 on timing of delivery of the pacing therapy, as described below. The sensed event signals produced by sensing circuit 86 may also be used by control circuit 80 to control the timing of pacing pulses delivered by therapy delivery circuit 84.

R-wave sensed event signals generated by sensing circuit 86 may cause control circuit 80 to withhold a scheduled ventricular pacing pulse and/or start a V-V pacing escape interval. R-wave sensed event signals may also be used by control circuit 80 for determining RR intervals (RRIs) for detecting tachyarrhythmia and determining a need for therapy. An RRI is the time interval between consecutively sensed R-waves and may be determined between consecutive R-wave sensed event signals received from sensing circuit 86. For example, control circuit 80 may include a timing circuit for determining RRIs between consecutive R-wave sensed event signals received from sensing circuit 86 and PP intervals between consecutive P-wave sensed event signals. R-wave and P-wave sensed event signals are also used for controlling various timers and/or counters used to control the timing of therapy delivery by therapy delivery circuit 84. The timing circuit may additionally set time windows such as the timing window described below, and/or morphology template windows, morphology analysis windows, P-wave sensing windows, blanking periods, R-wave sensing windows, pacing escape intervals including A-V and V-V intervals or perform other timing related functions of ICD 14 including synchronizing cardioversion shocks or other therapies delivered by therapy delivery circuit 84 with sensed cardiac events.

Therapy delivery circuit 84 includes charging circuitry, one or more charge storage devices, such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when ATP or other cardiac pacing pulses are delivered. For example, the timing circuit of control circuit 80 may include programmable digital counters set by a microprocessor of the control circuit 80 for controlling the basic time intervals associated with ventricular pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

Memory 82 may include read-only memory (ROM) in which stored programs controlling the operation of the control circuit 80 reside. Memory 82 may further include random access memory (RAM) or other memory devices configured as a number of recirculating buffers capable of holding a series of measured PP intervals, RR intervals, counts or other data for analysis by control circuit 80 for controlling therapy delivery.

Control parameters utilized by control circuit 80 for detecting cardiac rhythms and controlling therapy delivery may be programmed into memory 82 via telemetry circuit 88. Telemetry circuit 88 includes a transceiver and antenna for communicating with the leadless pacing device 100 or with external device 40 (shown in FIG. 1) using RF communication as described above. Under the control of control circuit 80, telemetry circuit 88 may receive downlink telemetry from and send uplink telemetry to leadless pacing device 100 and/or external device 40.

Figure 5:
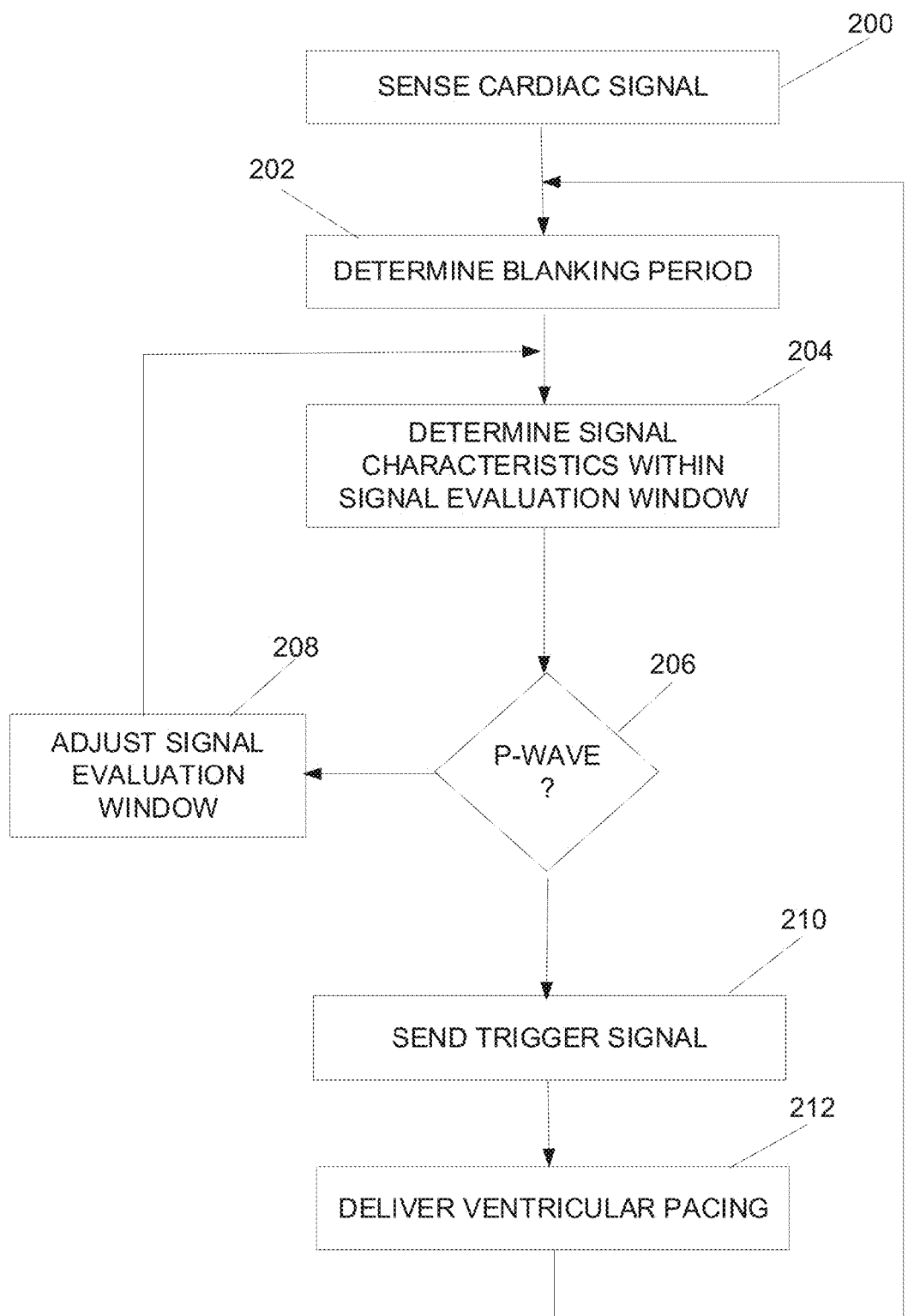
FIG. 5 is a flowchart of a method of delivering a cardiac pacing therapy in a leadless pacing device system according to an example of the present disclosure.

FIG. 5 is a flowchart of a method of delivering a cardiac pacing therapy in a leadless pacing device system according to an example of the present disclosure. As illustrated in FIG. 5, in one example of a method for delivering a leadless pacing therapy in a leadless pacing device system according to the present disclosure, the ICD 14 senses a far-field cardiac signal between the housing 15 and one of electrodes 24, 26 28, 30, 31 via sensing circuit 86, Block 200, for example. The control circuit 80 of the ICD 14 determines a blanking period, Block 202, based on the sensed cardiac signal. For example, the control circuit 80 may initially sense two or more intrinsic ventricular events and determine the blanking period based on the current cycle-length associated with the sensed intrinsic ventricular events. The blanking period may be made longer for slower heart rates or longer cycle-lengths. In one example, the blanking period is determined to be 1040 milliseconds if the cycle length is greater than or equal to 1280 milliseconds, 700 milliseconds if the cycle length is between 1000 milliseconds and 1280 milliseconds, 640 milliseconds if the cycle length is between 800 milliseconds and 1000 milliseconds, and 500 milliseconds if the cycle length is less than 800 milliseconds. The blanking period is subsequently updated for each cardiac cycle for delivering a ventricular pacing therapy during the cardiac cycle, as described below.

The control circuit 80 then determines signal characteristics of the sensed cardiac signal within a signal evaluation window, Block 204, that initially begins at the end of the blanking period. Based on the determined signal characteristics within the signal evaluation window, the control circuit 80 determines whether a P-wave has occurred, Block 206. If a P-wave is not determined to occur, No in Block 206, the control circuit 80 adjusts the signal evaluation window, Block 208. The signal characteristics of the sensed cardiac signal within the adjusted signal evaluation window are determined, Block 204, and a determination of whether a P-wave occurs, Block 206, for the adjusted signal evaluation window.

If a P-wave is not detected within the current signal evaluation window, the control circuit 80 adjusts the current signal evaluation window by advancing the window along the cardiac signal of the current cardiac cycle, Block 208, and the process is repeated for the adjusted signal evaluation window within the same cardiac cycle. If a P-wave is determined to occur, Yes in Block 206, the ICD 14 transmits a trigger signal via telemetry circuit 88 to the leadless pacing device 100, Block 210, instructing the leadless pacing device 100 to deliver pacing therapy at a predetermined interval following the sensed P-wave event, Block 212. The leadless pacing device 100 receives the trigger signal via the telemetry circuit 116, and control circuit 106 of leadless pacing device 100 delivers the pacing therapy at the predetermined interval via pulse generator 112 and electrodes 162 and 164. In some examples, the interval for delivering the ventricular pacing after the determined P-wave may be adjusted depending upon the signal characteristics. For example, if the device is performing adaptive CRT pacing, where periodically, for e.g. once a minute, the device may not pace after sensing a P-wave and instead measure the intrinsic AV sensing interval by determining the interval between the sensed P-wave and the sensed ventricular event. The interval for delivering V pace after the subsequent determined P-waves may be adjusted (this interval could be for example a certain percentage e.g. 60% of the interval between sensed P-wave and sensed intrinsic ventricular event).

Figure 6A:
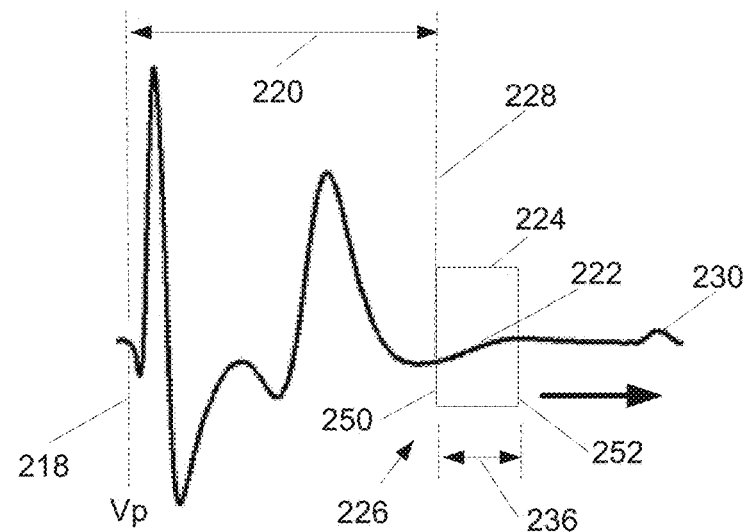
FIGS. 6A-C are graphical illustrations of determining signal characteristics in a method of delivering a cardiac pacing therapy in a leadless pacing device system according to an example of the present disclosure.
Figure 6B:
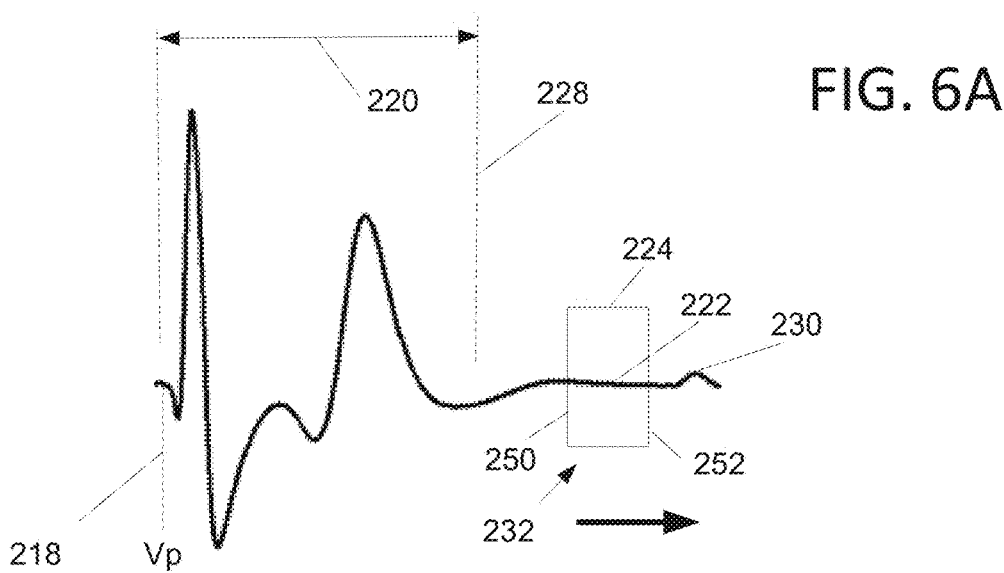
Figure 6C:
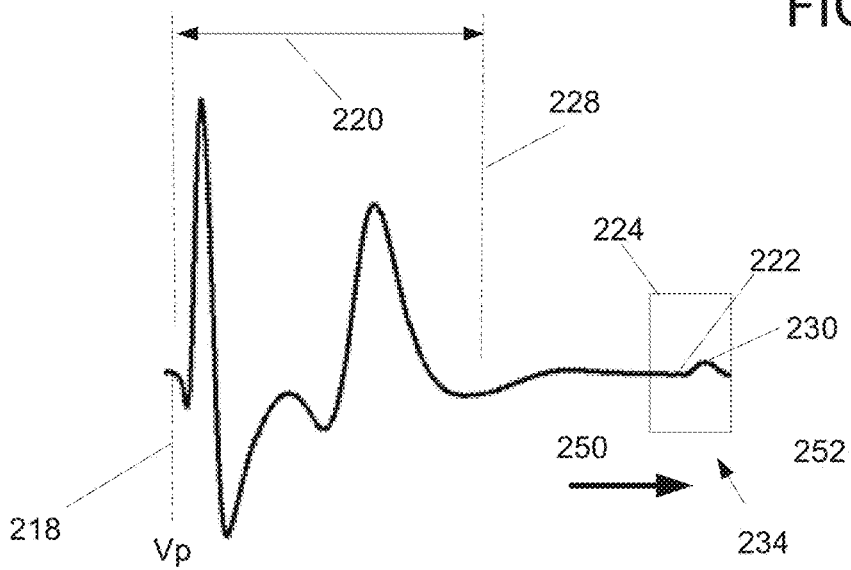

FIGS. 6A-C are graphical illustrations of determining signal characteristics in a method of delivering a cardiac pacing therapy in a leadless pacing device system according to an example of the present disclosure. As illustrated in FIGS. 6A-C, after the delivery of the ventricular pacing Vp therapy 218 by the leadless pacing device 100 for a given cardiac cycle, the processor 80 of the ICD 14 waits for a predetermined time period 220 subsequent to the delivered pacing, known as a blanking period. The time period 220 associated with the blanking period is typically programmable, and in one example the blanking period 220 may be initially determined based on the current cycle-length associated with sensed intrinsic ventricular events. For example, the blanking period 220 may be determined to be 1040 milliseconds if the cycle length is greater than or equal to 1280 milliseconds, 700 milliseconds if the cycle length is between 1000 milliseconds and 1280 milliseconds, 640 milliseconds if the cycle length is between 800 milliseconds and 1000 milliseconds, and 500 milliseconds if the cycle length is less than 800 milliseconds. The blanking period may be subsequently adjusted during delivery of a ventricular pacing therapy for each cardiac cycle, as described below. In another example, the blanking period may be held constant at a certain value for example, 500 ms, 520 ms, 540 ms, 560 ms, following a sensed or paced ventricular event.

Once the blanking period 220 has expired, the control circuit 80 determines signal characteristics of a sensed cardiac signal 222, Block 204 of FIG. 5. For example, the control circuit 80 determines amplitudes of the cardiac signal 222 within a signal evaluation window 224 that is initially located a first position 226, illustrated in FIG. 6A, relative to an end 228 of the blanking period 220 that follows the ventricular pace Vp event 218 for the cardiac cycle. Based on the amplitudes of the cardiac signal 222 within the currently positioned window 224, the control circuit 80 determines whether a P-wave 230 is detected. If the P-wave 230 is not detected based on the amplitudes of the signal 220 within the current window 224 at the first position 226, the control circuit 80 adjusts the current window 224, Block 208 of FIG. 5, by advancing the window 224 along the sensed cardiac signal 222 from the current position 226 to a next position 232 relative to the end 228 of the blanking period 226, illustrated in FIG. 6B.

The control circuit 80 then determines amplitudes of the cardiac signal 220 within the window 222 positioned at the second position 232 and determines whether the P-wave 232 is detected based on the amplitudes determined within the window 222 positioned at the second position 232. The process is repeated until the window 222 is adjusted to a position 234 along the sensed signal 222 in which the amplitudes determined within the window 224 along the sensed cardiac signal 220 satisfy an amplitude threshold, and therefore indicate that a P-wave is determined to occur, Yes in Block 206 of FIG. 5.

In one example, the signal evaluation window 224 may be set at a constant width 236, such as 80 milliseconds, or 40 milliseconds, for example. In another example, the width 236 of the window 224 may also be adjusted as the window 224 is adjusted between positions along the cardiac signal 220. For example, the width 236 may be reduced as the window 224 advances away from the end 228 of the blanking period 220. In another example, the reduction of the width 236 may be dependent upon the cycle length associated with two consecutive determined P-waves 230. For example, if the cycle length is reduced relative to the cycle length from the previous cardiac cycle, the width 236 of the window 224 may also be reduced. On the other hand, if the cycle length is increased relative to the cycle length from the previous cardiac cycle, the width 236 of the window 224 may also be increased.

In one example, initially, at greater cycle-lengths CL (>800 ms) a larger width 236 may be utilized so that longer windows (e.g. 100 ms) are utilized in the beginning, and the width 236 of the window 224 is subsequently reduced as the remaining portion of the cycle length gets shorter, until a certain minimum width 236 is reached. For example, the width 236 may be reduced in such a way that it reaches a minimum value, such as 40 ms, when within the window 224 is positioned within 100 ms of the end of the cycle length, or in other words when the window 224 is positioned at CL-100 ms. In this way, the width 236 of the window 224 is reduced when there is a higher expectation of occurrence of the next P-wave. In another example, the window 224 may maintain the same width 236 (i.e., 40 ms) but may be adjusted to be advanced in steps of 100 ms (non-overlapping) and subsequently reduced to overlapping advancements in smaller increments of 1 ms, 5 ms, 10 ms, when within 100 ms of the next expected P-wave (or when at CL-100 ms following the last sensed P-wave).

In one example, the window 224 may be advanced along the cardiac signal along the cardiac signal 222 so as to begin at the end of the previously positioned window. In another example, the window 224 may be advanced along the cardiac signal 222 so that the current window 224 and the previous window 224 overlap.

Figure 7:
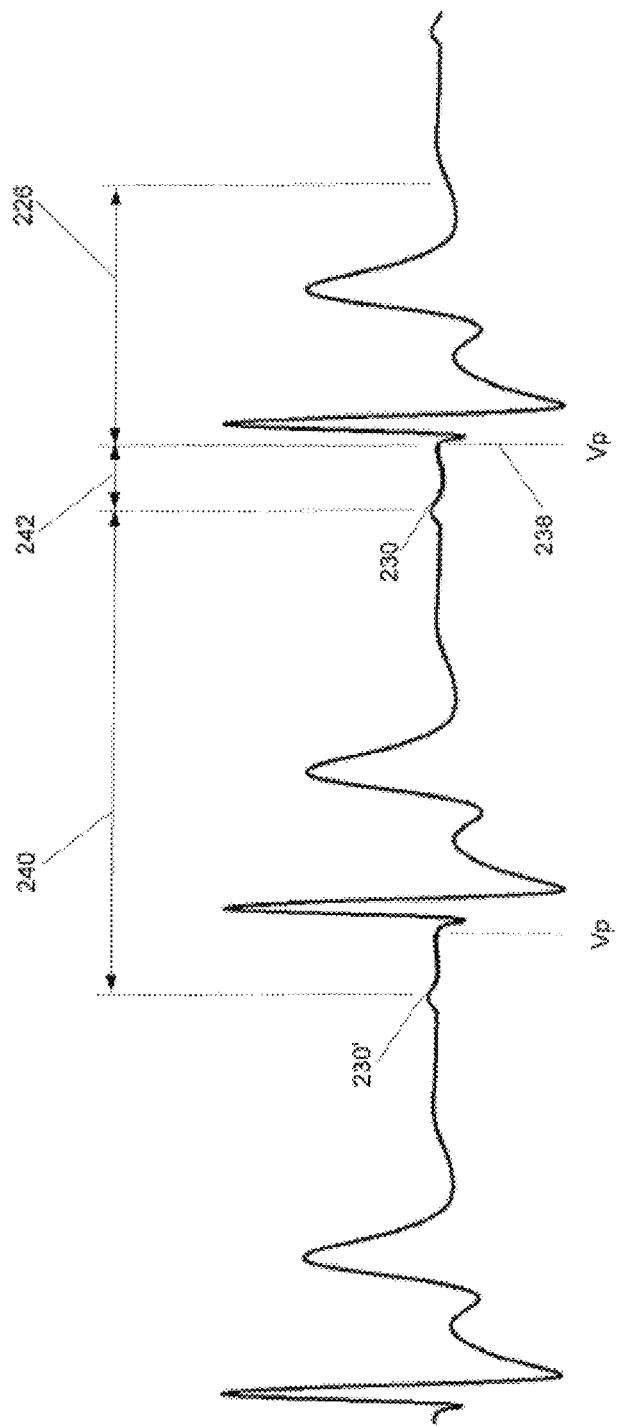
FIG. 7 is a graphical illustration of determining signal characteristics in a method of delivering a cardiac pacing therapy in a leadless pacing device system according to an example of the present disclosure.

FIG. 7 is a graphical illustration of determining signal characteristics in a method of delivering a cardiac pacing therapy in a leadless pacing device system according to an example of the present disclosure. As illustrated in FIG. 7, once a P-wave 230 is determined to occur for a given cardiac cycle, the ICD 14 transmits a trigger signal to the leadless pacing device 100 instructing the leadless pacing device 100 on timing of delivery of the pacing therapy relative to the determined P-wave 230 so that leadless pacing device 100 delivers a ventricular pacing therapy Vp 238 at a predetermined time interval 242 relative to the P-wave 230. The control circuit 80 then determines a cycle length 240 indicative of an A-A interval extending between the current determined P-wave 230 and a previous P-wave 230' determined prior to the current determined P-wave 230.

The blanking period 226 for the current delivered pacing therapy 238 is then determined based on the current determined cycle length 240. For example, as described above, the blanking period 226 may be determined to be 1040 milliseconds if the cycle length 240 is greater than or equal to 1280 milliseconds, 700 milliseconds if the cycle length 240 is between 1000 milliseconds and 1280 milliseconds, 640 milliseconds if the cycle length 240 is between 800 milliseconds and 1000 milliseconds, and 500 milliseconds if the cycle length 240 is less than 800 milliseconds. The process is then repeated for the next cardiac cycle.

In this way, a cardiac pacing device system may include a substernal or subcutaneous device 14 positioned extravascularly within the patient and a leadless pacing device 100 positioned in the left ventricle, the right ventricle or both the left ventricle and the right ventricle of the patient. The substernal or subcutaneous device 14 senses an atrial activation from far-field vectors, determines desired features or portions of the cardiac signal, and triggers delivery of the pacing therapy by the leadless pacing device 100 based on the determined portion of the signal having the desired signal feature. One of the signal features may be a portion of the signal in which an atrial activation, or P-wave is determined to occur. Since an atrial activation, or P-wave, has a much lower signal amplitude relative to other cardiac signal components of a cardiac cycle, such as QRS and T-wave components, far-field sensing of the atrial activation via substernal or subcutaneous positioned sensing electrodes may be problematic.

Therefore, the present disclosure describes a cardiac pacing system and method that includes sensing an atrial activation from substernal or subcutaenous ECG signals. The method includes tracking amplitude features of a cardiac signal as sensing of a cardiac signal for a given cardiac cycle occurs. If the amplitude features of the cardiac signal within a signal evaluation window do not meet a predetermined threshold, the time-window is advanced across the sensed cardiac signal for the same sensed cardiac cycle, and the process is repeated. On the other hand, if one or more of the features meet the predetermined threshold, an atrial event is determined to be sensed and a triggering signal may be transmitted from the substernal or subcutaneous 14 to the leadless pacing device 100 in the ventricle, instructing the leadless pacing device 100 to pace at a predetermined time interval following the sensed atrial event.

Figure 8:
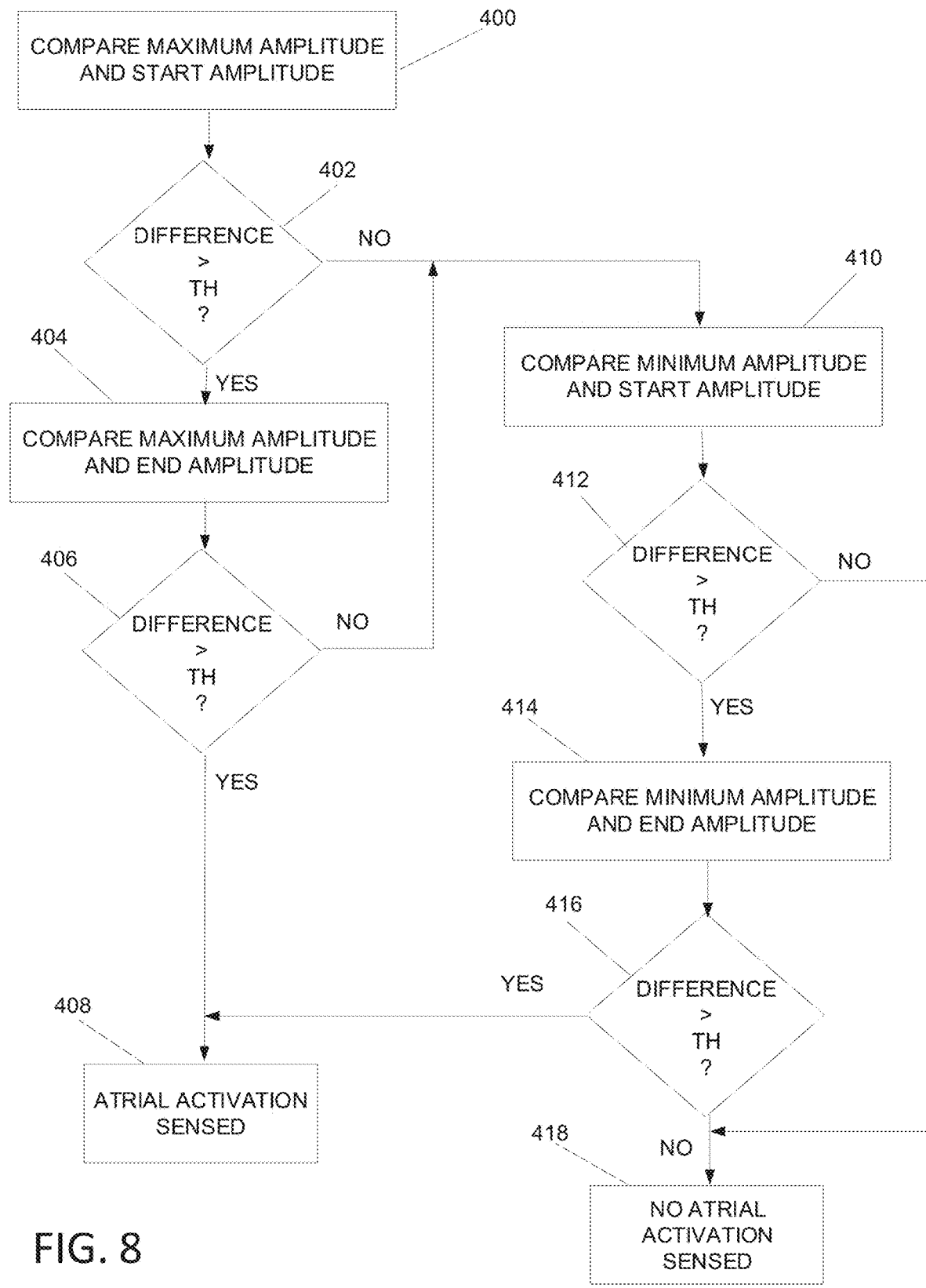
FIG. 8 is a flowchart of determining signal characteristics in a method of delivering a cardiac pacing therapy in a leadless pacing device system according to an example of the present disclosure.

FIG. 8 is a flowchart of determining signal characteristics in a method of delivering a cardiac pacing therapy in a leadless pacing device system according to an example of the present disclosure. As described above, in one example of a method for delivering a leadless pacing therapy according to the present disclosure, during the determination of signal characteristics of a sensed cardiac signal 222, Block 204 of FIG. 5, the ICD 14 begins by determining amplitudes of the cardiac signal 222 within the signal evaluation window 224 initially located at the first position 226, illustrated in FIG. 6A, relative to an end 228 of the blanking period 220 following the ventricular pace Vp event 218. For example, as illustrated in FIG. 6A, the control circuit 80 may determine an amplitude of the cardiac signal 222 at a start 250 of the window 224 and at an end 252 of the window 224, along with a maximum amplitude of the signal 222 and a minimum amplitude of the signal 222 within the window 224.

As illustrated in FIG. 8, once amplitudes of the cardiac signal 222 within the signal evaluation window 224 are determined, the control circuit 80 may compare the maximum amplitude of the signal 222 within the window 224 and the amplitude of the cardiac signal 222 at the start 250 of the window 224, Block 400, and determine whether a difference between the maximum amplitude of the signal 222 within the window 224 and the amplitude of the cardiac signal 222 at the start 250 of the window 224 is greater than an amplitude threshold, Block 402.

According to one example, the amplitude threshold may be set as a value between 0.010 mV and 0.090 mV. The amplitude threshold may be set as a percentage (e.g. 10%, 20%, 30%, 40%, 50%) of the P-wave amplitude measured between electrodes on the substernal or subcutaneous ICD lead. The device may conduct periodic measurement of P-wave amplitudes and accordingly adjust the amplitude threshold. The P-wave amplitude may be automatically measured by the device setting a window around a sensed P-wave (e.g. 50 ms, 100 ms wide window centered on the sensed P-wave) and determining the peak-to-peak amplitude or difference between the maximum amplitude and the minimum amplitude of the sensed P-wave.

As an illustration, if the amplitude threshold is set as 0.045 mV, the control circuit 80 may determine in Block 402 whether the maximum amplitude, $A_{max}$, of the signal 222 within the window 224 minus the amplitude of the cardiac signal 222 at the start 250, $A_{start}$, of the window 224 is greater than 0.045 mV. If the difference $A_{max}-A_{start}$ is greater than the amplitude threshold, Yes in Block 402, the control circuit 80 may compare the maximum amplitude of the signal 222 within the window 224 and the amplitude of the cardiac signal 222 at the end 252 of the window 224, Block 404, and determine whether a difference between the maximum amplitude of the signal 222 within the window 224 and the amplitude of the cardiac signal 222 at the end 252 of the window 224, $A_{end}$, is greater than the amplitude threshold, Block 406.

If the difference $A_{max}-A_{end}$ is greater than the amplitude threshold, Yes in Block 406, the control circuit 80 determines that the P-wave 230 is determined, Block 408, and the ICD 14 transmits a trigger signal via telemetry circuit 88 to the leadless pacing device 100 instructing the leadless pacing device 100 to deliver pacing therapy at a predetermined interval following the sensed P-wave event 230. The leadless pacing device 100 receives the trigger signal via telemetry circuit 116, and control circuit 106 of leadless pacing device 100 delivers the pacing therapy at the predetermined interval via pulse generator 112 and electrodes 162 and 164, as described above.

If either the difference $A_{max}-A_{start}$ is not greater than the amplitude threshold, No in Block 402, or the difference $A_{max}-A_{end}$ is not greater than the amplitude threshold, No in Block 406, the control circuit 80 may compare the minimum amplitude $A_{min}$ of the cardiac signal 222 within the window 224 and the amplitude of the cardiac signal 222 at the start 250 of the window 224, Block 410, and determine whether a difference between the minimum amplitude of the signal 222 within the window 224 and the amplitude of the cardiac signal 222 at the start 250 of the window 224 is greater than the amplitude threshold, Block 412.

If the difference $A_{start}-A_{min}$ is greater than the amplitude threshold, Yes in Block 412, the control circuit 80 may compare the minimum amplitude of the cardiac signal 222 within the window 224 and the amplitude of the cardiac signal 222 at the end 252 of the window 224, Block 414, and determine whether a difference between the minimum amplitude of the signal 222 within the window 224 and the amplitude of the cardiac signal 222 at the end 252 of the window 224, is greater than the amplitude threshold, Block 416. If the difference $A_{end}-A_{min}$ is greater than the amplitude threshold, Yes in Block 416, the control circuit 80 determines that the P-wave 230 is sensed, Block 408, and the ICD 14 transmits a trigger signal via telemetry circuit 88 to the leadless pacing device 100 instructing the leadless pacing device 100 to deliver pacing therapy at a predetermined interval following the sensed P-wave event 230. The leadless pacing device 100 receives the trigger signal via telemetry circuit 116, and control circuit 106 of leadless pacing device 100 delivers the pacing therapy at the predetermined interval via pulse generator 112 and electrodes 162 and 164, as described above.

If either the difference $A_{start}-A_{min}$ is not greater than the amplitude threshold, No in Block 412, or the difference $A_{end}-A_{min}$ is not greater than the amplitude threshold, No in Block 416, the control circuit 80 determines that the P-wave 230 is not sensed, Block 418, the control circuit adjusts the signal evaluation window, determines the signal characteristics of the sensed cardiac signal within the adjusted signal evaluation window, and determines of whether a P-wave occurs for the adjusted signal evaluation window, as described above.

In this way, the control circuit 80 determines that a P-wave 230 is sensed during the current cardiac cycle if both the difference $A_{max}-A_{start}$ and the difference $A_{max}-A_{end}$ is greater than the amplitude threshold, or if both the difference $A_{start}-A_{min}$ and the difference $A_{end}-A_{min}$ is greater than the amplitude threshold. On the other hand, the control circuit 80 determines that a P-wave 230 is not sensed during the current cardiac cycle if both one or both of the difference $A_{max}-A_{start}$ and the difference $A_{max}-A_{end}$ is not greater than the amplitude threshold, and one or both of the difference $A_{start}-A_{min}$ and the difference $A_{end}-A_{min}$ is not greater than the amplitude threshold. Therefore, a P-wave is determined to be sensed if:

$A_{max}-A_{start}$>Amplitude Threshold AND $A_{max}-A_{end}$>Amplitude Threshold

OR $A_{start}-A_{min}$>Amplitude Threshold AND $A_{end}-A_{min}$>Amplitude Threshold In this way, a cardiac pacing device system may include a substernal or subcutaneous device 14 positioned extravascularly within the patient and a leadless pacing device 100 positioned in the left ventricle, the right ventricle or both the left ventricle and the right ventricle of the patient. The substernal or subcutaneous device 14 senses an atrial activation from far-field vectors, determines desired features or portions of the cardiac signal, and triggers delivery of the pacing therapy by the leadless pacing device 100 based on the determined portion of the signal having the desired signal feature. One of the signal features may be a portion of the signal in which an atrial activation, or P-wave is determined to occur. Since an atrial activation, or P-wave, has a much lower signal amplitude relative to other cardiac signal components of a cardiac cycle, such as QRS and T-wave components, far-field sensing of the atrial activation via substernal or subcutaneous positioned sensing electrodes may be problematic.

Therefore, the present disclosure describes a cardiac pacing system and method that includes sensing an atrial activation from substernal or subcutaenous ECG signals. The method includes tracking amplitude features of a cardiac signal as sensing of a cardiac signal for a given cardiac cycle occurs. If the amplitude of the cardiac signal within a signal evaluation window do not meet a predetermined threshold, the time-window is advanced across the sensed cardiac signal for the same sensed cardiac cycle, and the process is repeated. On the other hand, if one or more of the features meet the predetermined threshold, an atrial event is determined to be sensed and a triggering signal may be transmitted from the substernal or subcutaneous 14 to the leadless pacing device 100 in the ventricle, instructing the leadless pacing device 100 to pace at a predetermined time following the sensed atrial event.

The techniques described in this disclosure, including those attributed to the IMD 14, leadless pacing device 100, the programmer 40, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," "control circuit", or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATED EMBODIMENTS

Embodiment 1

A method of delivering a cardiac pacing therapy, comprising: sensing a cardiac signal; determining signal characteristics of the cardiac signal within a signal evaluation window positioned along a first portion of a cardiac cycle; determining whether a P-wave occurs within the signal evaluation window associated with the first portion of the same cardiac cycle in response to the determined signal characteristics; adjusting the signal evaluation window to be positioned along a second portion of the cardiac cycle in response to the P-wave not occurring within the signal evaluation window; determining signal characteristics of the cardiac signal within the signal evaluation window positioned along the second portion of the cardiac cycle; determining whether a P-wave occurs in response to the signal characteristics determined within the signal evaluation window positioned along the second portion of the cardiac cycle; and delivering ventricular pacing therapy in response to a P-wave being determined to occur.

Embodiment 2

The method of embodiment 1, further comprising: determining a cycle length between the P-wave determined for the cardiac cycle and a P-wave determined for a previous cardiac cycle; and adjusting a blanking period for subsequent delivery of ventricular pacing therapy in response to the determined cycle length.

Embodiment 3

The method of any of embodiments 1 and 2, further comprising: determining a cycle length between the P-wave determined for the cardiac cycle and a P-wave determined for a previous cardiac cycle; and adjusting a width of the signal evaluation window in response to the determined cycle length.

Embodiment 4

The method of any of embodiments 1-3, further comprising: determining whether a first difference between a maximum amplitude of the cardiac signal within the signal evaluation window and an amplitude of the cardiac signal at a start of the signal evaluation window is greater than an amplitude threshold; determining whether a second difference between the maximum amplitude of the cardiac signal within the signal evaluation window and an amplitude of the cardiac signal at an end of the signal evaluation window is greater than the amplitude threshold; and determining a P-wave occurs within the signal evaluation window in response to both the first difference and the second difference being greater than the amplitude threshold.

Embodiment 5

The method of embodiment 4, further comprising determining a P-wave does not occur within the signal evaluation window in response to at least one of the first difference and the second difference not being greater than the amplitude threshold.

Embodiment 6

The method of any of embodiments 1-5, further comprising: determining whether a first difference between an amplitude of the cardiac signal at a start of the signal evaluation window and a minimum amplitude of the cardiac signal within the signal evaluation window and is greater than an amplitude threshold; determining whether a second difference between an amplitude of the cardiac signal at an end of the signal evaluation window and the minimum amplitude of the cardiac signal within the signal evaluation window is greater than the amplitude threshold; and determining a P-wave occurs within the signal evaluation window in response to both the first difference and the second difference being greater than the amplitude threshold.

Embodiment 7

The method of embodiment 6, further comprising determining a P-wave does not occur within the signal evaluation window in response to at least one of the first difference and the second difference not being greater than the amplitude threshold.

Embodiment 8

The method of any of embodiments 1-5 and 7, further comprising: determining whether a first difference between a maximum amplitude of the cardiac signal within the signal evaluation window and an amplitude of the cardiac signal at a start of the signal evaluation window is greater than an amplitude threshold; determining whether a second difference between the maximum amplitude of the cardiac signal within the signal evaluation window and an amplitude of the cardiac signal at an end of the signal evaluation window is greater than the amplitude threshold; determining whether a third difference between the amplitude of the cardiac signal at the start of the signal evaluation window and a minimum amplitude of the cardiac signal within the signal evaluation window and is greater than the amplitude threshold; determining whether a fourth difference between the amplitude of the cardiac signal at the end of the signal evaluation window and the minimum amplitude of the cardiac signal within the signal evaluation window is greater than the amplitude threshold; and determining a P-wave occurs within the signal evaluation window in response to one of both the first difference and the second difference being greater than the amplitude threshold, and both the third difference and the fourth difference being greater than the amplitude threshold.

Embodiment 9

The method of embodiment 8, further comprising determining a P-wave does not occur within the signal evaluation window in response to both the first difference and the second difference not being greater than the amplitude threshold and both the third difference and fourth difference not being greater than the amplitude threshold.

Embodiment 10

The method of any of embodiments 1-9, further comprising: determining a cycle length between the P-wave determined for the cardiac cycle and a P-wave determined for a previous cardiac cycle; and adjusting a blanking period for subsequent delivery of ventricular pacing therapy in response to the determined cycle length.

Embodiment 11

The method of any of embodiments 1-10, further comprising: determining a cycle length between the P-wave determined for the cardiac cycle and a P-wave determined for a previous cardiac cycle; and adjusting a width of the signal evaluation window in response to the determined cycle length.

Embodiment 12

A cardiac pacing system for delivering a cardiac pacing therapy, comprising: an implantable cardioverter defibrillator (ICD), the ICD comprising a housing; a lead having a lead body and electrically coupled to the housing of the ICD; a plurality of electrodes positioned along the lead body; a control circuit positioned within the housing of the ICD and configured to determine a cardiac signal sensed between two electrodes of the plurality of electrodes positioned along the lead body or between the housing of the ICD and an electrode of the plurality of electrodes positioned along the lead body, determine signal characteristics of the cardiac signal within a signal evaluation window positioned along a first portion of a cardiac cycle, determine whether a P-wave occurs within the signal evaluation window associated with the first portion of the cardiac cycle in response to the determined signal characteristics, adjust the signal evaluation window to be positioned along a second portion of the cardiac cycle in response to the P-wave not occurring within the signal evaluation window, determine signal characteristics of the cardiac signal within the signal evaluation window positioned along the second portion of the cardiac cycle, determine whether a P-wave occurs in response to the signal characteristics determined within the signal evaluation window positioned along the second portion of the cardiac cycle, and deliver a trigger signal in response to a P-wave being determined to occur; a leadless pacing device comprising a housing; a plurality of electrodes positioned along the housing of the leadless pacing device; and a control circuit positioned within the housing of the leadless pacing device and configured to receive the trigger signal from the ICD and deliver a ventricular pacing therapy via the plurality of electrodes positioned along the housing of the leadless pacing device.

Embodiment 13

The cardiac pacing system of embodiment 12, wherein the control circuit positioned within the housing of the ICD is configured to determine a cycle length between the P-wave determined for the cardiac cycle and a P-wave determined for a previous cardiac cycle, and adjust a blanking period for subsequent delivery of ventricular pacing therapy in response to the determined cycle length.

Embodiment 14

The cardiac pacing system of any of embodiments 12 and 13, wherein the control circuit positioned within the housing of the ICD is configured to determine a cycle length between the P-wave determined for the cardiac cycle and a P-wave determined for a previous cardiac cycle, and adjust a width of the signal evaluation window in response to the determined cycle length.

Embodiment 15

The cardiac pacing system of any of embodiment 12-14, wherein the control circuit positioned within the housing of the ICD is configured to determine whether a first difference between a maximum amplitude of the cardiac signal within the signal evaluation window and an amplitude of the cardiac signal at a start of the signal evaluation window is greater than an amplitude threshold, determine whether a second difference between the maximum amplitude of the cardiac signal within the signal evaluation window and an amplitude of the cardiac signal at an end of the signal evaluation window is greater than the amplitude threshold, and determine a P-wave occurs within the signal evaluation window in response to both the first difference and the second difference being greater than the amplitude threshold.

Embodiment 16

The cardiac pacing system of any of embodiments 12-15, wherein the control circuit positioned within the housing of the ICD is configured to determine a P-wave does not occur within the signal evaluation window in response to at least one of the first difference and the second difference not being greater than the amplitude threshold.

Embodiment 17

The cardiac pacing system of any of embodiments 12-16, wherein the control circuit positioned within the housing of the ICD is configured to determine whether a first difference between an amplitude of the cardiac signal at a start of the signal evaluation window and a minimum amplitude of the cardiac signal within the signal evaluation window and is greater than an amplitude threshold, determine whether a second difference between an amplitude of the cardiac signal at an end of the signal evaluation window and the minimum amplitude of the cardiac signal within the signal evaluation window is greater than the amplitude threshold, and determine a P-wave occurs within the signal evaluation window in response to both the first difference and the second difference being greater than the amplitude threshold.

Embodiment 18

The cardiac pacing system of embodiment 17, wherein the control circuit positioned within the housing of the ICD is configured to determine a P-wave does not occur within the signal evaluation window in response to at least one of the first difference and the second difference not being greater than the amplitude threshold.

Embodiment 19

The cardiac pacing system of any of embodiment 12-18, wherein the control circuit positioned within the housing of the ICD is configured to determine whether a first difference between a maximum amplitude of the cardiac signal within the signal evaluation window and an amplitude of the cardiac signal at a start of the signal evaluation window is greater than an amplitude threshold, determine whether a second difference between the maximum amplitude of the cardiac signal within the signal evaluation window and an amplitude of the cardiac signal at an end of the signal evaluation window is greater than the amplitude threshold, determine whether a third difference between the amplitude of the cardiac signal at the start of the signal evaluation window and a minimum amplitude of the cardiac signal within the signal evaluation window and is greater than the amplitude threshold, determine whether a fourth difference between the amplitude of the cardiac signal at the end of the signal evaluation window and the minimum amplitude of the cardiac signal within the signal evaluation window is greater than the amplitude threshold, and determine a P-wave occurs within the signal evaluation window in response to one of both the first difference and the second difference being greater than the amplitude threshold, and both the third difference and the fourth difference being greater than the amplitude threshold.

Embodiment 20

The cardiac pacing system of embodiment 19, wherein the control circuit positioned within the housing of the ICD is configured to determine a P-wave does not occur within the signal evaluation window in response to both the first difference and the second difference not being greater than the amplitude threshold and both the third difference and fourth difference not being greater than the amplitude threshold.

Embodiment 21

The cardiac pacing system of any of embodiments 12-20, wherein the control circuit positioned within the housing of the ICD is configured to determine a cycle length between the P-wave determined for the cardiac cycle and a P-wave determined for a previous cardiac cycle, and adjust a blanking period for subsequent delivery of ventricular pacing therapy in response to the determined cycle length.

Embodiment 22

The cardiac pacing system of any of claims 12-21, wherein the control circuit positioned within the housing of the ICD is configured to determine a cycle length between the P-wave determined for the cardiac cycle and a P-wave determined for a previous cardiac cycle, and adjust a width of the signal evaluation window in response to the determined cycle length.

Embodiment 23

A non-transitory computer readable medium storing instructions which cause a cardiac pacing device system to perform a method comprising: sensing a cardiac signal; determining signal characteristics of the cardiac signal within a signal evaluation window positioned along a first portion of a cardiac cycle; determining whether a P-wave occurs within the signal evaluation window associated with the first portion of the cardiac cycle in response to the determined signal characteristics; adjusting the signal evaluation window to be positioned along a second portion of the cardiac cycle in response to the P-wave not occurring within the signal evaluation window; determining signal characteristics of the cardiac signal within the signal evaluation window positioned along the second portion of the cardiac cycle; determining whether a P-wave occurs in response to the signal characteristics determined within the signal evaluation window positioned along the second portion of the cardiac cycle; and delivering ventricular pacing therapy in response to a P-wave being determined to occur.

What is claimed:
1. A method of delivering a cardiac pacing therapy, comprising:
   sensing a cardiac signal;
   determining signal characteristics of the cardiac signal within a signal evaluation window positioned along a first portion of a cardiac cycle;

determining whether a P-wave occurs within the signal evaluation window associated with the first portion of the cardiac cycle in response to the determined signal characteristics;
adjusting the signal evaluation window to be positioned along a second portion of the cardiac cycle in response to the P-wave not occurring within the signal evaluation window;
determining signal characteristics of the cardiac signal within the signal evaluation window positioned along the second portion of the cardiac cycle;
determining whether a P-wave occurs in response to the signal characteristics determined within the signal evaluation window positioned along the second portion of the cardiac cycle; and
delivering ventricular pacing therapy in response to a P-wave being determined to occur.

2. The method of claim 1, further comprising:
determining a cycle length between the P-wave determined for the cardiac cycle and a P-wave determined for a previous cardiac cycle; and
adjusting a blanking period for subsequent delivery of ventricular pacing therapy in response to the determined cycle length.

3. The method of claim 1, further comprising:
determining a cycle length between the P-wave determined for the cardiac cycle and a P-wave determined for a previous cardiac cycle; and
adjusting a width of the signal evaluation window in response to the determined cycle length.

4. The method of claim 1, further comprising:
determining whether a first difference between a maximum amplitude of the cardiac signal within the signal evaluation window and an amplitude of the cardiac signal at a start of the signal evaluation window is greater than an amplitude threshold;
determining whether a second difference between the maximum amplitude of the cardiac signal within the signal evaluation window and an amplitude of the cardiac signal at an end of the signal evaluation window is greater than the amplitude threshold; and
determining a P-wave occurs within the signal evaluation window in response to both the first difference and the second difference being greater than the amplitude threshold.

5. The method of claim 4, further comprising determining a P-wave does not occur within the signal evaluation window in response to at least one of the first difference and the second difference not being greater than the amplitude threshold.

6. The method of claim 1, further comprising:
determining whether a first difference between an amplitude of the cardiac signal at a start of the signal evaluation window and a minimum amplitude of the cardiac signal within the signal evaluation window and is greater than an amplitude threshold;
determining whether a second difference between an amplitude of the cardiac signal at an end of the signal evaluation window and the minimum amplitude of the cardiac signal within the signal evaluation window is greater than the amplitude threshold; and
determining a P-wave occurs within the signal evaluation window in response to both the first difference and the second difference being greater than the amplitude threshold.

7. The method of claim 6, further comprising determining a P-wave does not occur within the signal evaluation window in response to at least one of the first difference and the second difference not being greater than the amplitude threshold.

8. The method of claim 1, further comprising:
determining whether a first difference between a maximum amplitude of the cardiac signal within the signal evaluation window and an amplitude of the cardiac signal at a start of the signal evaluation window is greater than an amplitude threshold;
determining whether a second difference between the maximum amplitude of the cardiac signal within the signal evaluation window and an amplitude of the cardiac signal at an end of the signal evaluation window is greater than the amplitude threshold;
determining whether a third difference between the amplitude of the cardiac signal at the start of the signal evaluation window and a minimum amplitude of the cardiac signal within the signal evaluation window and is greater than the amplitude threshold;
determining whether a fourth difference between the amplitude of the cardiac signal at the end of the signal evaluation window and the minimum amplitude of the cardiac signal within the signal evaluation window is greater than the amplitude threshold; and
determining a P-wave occurs within the signal evaluation window in response to one of both the first difference and the second difference being greater than the amplitude threshold, and both the third difference and the fourth difference being greater than the amplitude threshold.

9. The method of claim 8, further comprising determining a P-wave does not occur within the signal evaluation window in response to both the first difference and the second difference not being greater than the amplitude threshold and both the third difference and fourth difference not being greater than the amplitude threshold.

10. The method of claim 9, further comprising:
determining a cycle length between the P-wave determined for the cardiac cycle and a P-wave determined for a previous cardiac cycle; and
adjusting a blanking period for subsequent delivery of ventricular pacing therapy in response to the determined cycle length.

11. The method of claim 9, further comprising:
determining a cycle length between the P-wave determined for the cardiac cycle and a P-wave determined for a previous cardiac cycle; and
adjusting a width of the signal evaluation window in response to the determined cycle length.

12. A cardiac pacing system for delivering a cardiac pacing therapy, comprising:
an implantable cardioverter defibrillator (ICD), the ICD comprising a housing;
a lead having a lead body and electrically coupled to the housing of the ICD;
a plurality of electrodes positioned along the lead body;
a control circuit positioned within the housing of the ICD and configured to determine a cardiac signal sensed between two electrodes of the plurality of electrodes positioned along the lead body or between the housing of the ICD and an electrode of the plurality of electrodes positioned along the lead body, determine signal characteristics of the cardiac signal within a signal evaluation window positioned along a first portion of a cardiac cycle, determine whether a P-wave occurs within the signal evaluation window associated with the first portion of the cardiac cycle in response to the determined signal characteristics, adjust the signal evaluation window to be positioned along a second portion of the cardiac cycle in response to the P-wave not occurring within the signal evaluation window, determine signal characteristics of the cardiac signal within the signal evaluation window positioned along the second portion of the cardiac cycle, determine whether a P-wave occurs in response to the signal characteristics determined within the signal evaluation window positioned along the second portion of the cardiac cycle, and deliver a trigger signal in response to a P-wave being determined to occur;

a leadless pacing device comprising a housing;

a plurality of electrodes positioned along the housing of the leadless pacing device; and a control circuit positioned within the housing of the leadless pacing device and configured to receive the trigger signal from the ICD and deliver a ventricular pacing therapy via the plurality of electrodes positioned along the housing of the leadless pacing device.

13. The cardiac pacing system of claim 12, wherein the control circuit positioned within the housing of the ICD is configured to determine a cycle length between the P-wave determined for the cardiac cycle and a P-wave determined for a previous cardiac cycle, and adjust a blanking period for subsequent delivery of ventricular pacing therapy in response to the determined cycle length.

14. The cardiac pacing system of claim 12, wherein the control circuit positioned within the housing of the ICD is configured to determine a cycle length between the P-wave determined for the cardiac cycle and a P-wave determined for a previous cardiac cycle, and adjust a width of the signal evaluation window in response to the determined cycle length.

15. The cardiac pacing system of claim 12, wherein the control circuit positioned within the housing of the ICD is configured to determine whether a first difference between a maximum amplitude of the cardiac signal within the signal evaluation window and an amplitude of the cardiac signal at a start of the signal evaluation window is greater than an amplitude threshold, determine whether a second difference between the maximum amplitude of the cardiac signal within the signal evaluation window and an amplitude of the cardiac signal at an end of the signal evaluation window is greater than the amplitude threshold, and determine a P-wave occurs within the signal evaluation window in response to both the first difference and the second difference being greater than the amplitude threshold.

16. The cardiac pacing system of claim 15, wherein the control circuit positioned within the housing of the ICD is configured to determine a P-wave does not occur within the signal evaluation window in response to at least one of the first difference and the second difference not being greater than the amplitude threshold.

17. The cardiac pacing system of claim 12, wherein the control circuit positioned within the housing of the ICD is configured to determine whether a first difference between an amplitude of the cardiac signal at a start of the signal evaluation window and a minimum amplitude of the cardiac signal within the signal evaluation window and is greater than an amplitude threshold, determine whether a second difference between an amplitude of the cardiac signal at an end of the signal evaluation window and the minimum amplitude of the cardiac signal within the signal evaluation window is greater than the amplitude threshold, and determine a P-wave occurs within the signal evaluation window in response to both the first difference and the second difference being greater than the amplitude threshold.

18. The cardiac pacing system of claim 17, wherein the control circuit positioned within the housing of the ICD is configured to determine a P-wave does not occur within the signal evaluation window in response to at least one of the first difference and the second difference not being greater than the amplitude threshold.

19. The cardiac pacing system of claim 12, wherein the control circuit positioned within the housing of the ICD is configured to determine whether a first difference between a maximum amplitude of the cardiac signal within the signal evaluation window and an amplitude of the cardiac signal at a start of the signal evaluation window is greater than an amplitude threshold, determine whether a second difference between the maximum amplitude of the cardiac signal within the signal evaluation window and an amplitude of the cardiac signal at an end of the signal evaluation window is greater than the amplitude threshold, determine whether a third difference between the amplitude of the cardiac signal at the start of the signal evaluation window and a minimum amplitude of the cardiac signal within the signal evaluation window and is greater than the amplitude threshold, determine whether a fourth difference between the amplitude of the cardiac signal at the end of the signal evaluation window and the minimum amplitude of the cardiac signal within the signal evaluation window is greater than the amplitude threshold, and determine a P-wave occurs within the signal evaluation window in response to one of both the first difference and the second difference being greater than the amplitude threshold, and both the third difference and the fourth difference being greater than the amplitude threshold.

20. The cardiac pacing system of claim 19, wherein the control circuit positioned within the housing of the ICD is configured to determine a P-wave does not occur within the signal evaluation window in response to both the first difference and the second difference not being greater than the amplitude threshold and both the third difference and fourth difference not being greater than the amplitude threshold.

21. The cardiac pacing system of claim 20, wherein the control circuit positioned within the housing of the ICD is configured to determine a cycle length between the P-wave determined for the cardiac cycle and a P-wave determined for a previous cardiac cycle, and adjust a blanking period for subsequent delivery of ventricular pacing therapy in response to the determined cycle length.

22. The cardiac pacing system of claim 20, wherein the control circuit positioned within the housing of the ICD is configured to determine a cycle length between the P-wave determined for the cardiac cycle and a P-wave determined for a previous cardiac cycle, and adjust a width of the signal evaluation window in response to the determined cycle length.

23. A non-transitory computer readable medium storing instructions which cause a cardiac pacing device system to perform a method comprising:

sensing a cardiac signal;

determining signal characteristics of the cardiac signal within a signal evaluation window positioned along a first portion of a cardiac cycle;

determining whether a P-wave occurs within the signal evaluation window associated with the first portion of the cardiac cycle in response to the determined signal characteristics;

adjusting the signal evaluation window to be positioned along a second portion of the cardiac cycle in response to the P-wave not occurring within the signal evaluation window;

determining signal characteristics of the cardiac signal within the signal evaluation window positioned along the second portion of the cardiac cycle;

determining whether a P-wave occurs in response to the signal characteristics determined within the signal evaluation window positioned along the second portion of the cardiac cycle; and delivering ventricular pacing therapy in response to a P-wave being determined to occur.

\* \* \* \* \*